(12) United States Patent
Sakawa et al.

(10) Patent No.: US 7,007,543 B2
(45) Date of Patent: Mar. 7, 2006

(54) AIR-FUEL RATIO SENSOR

(75) Inventors: Toshihiro Sakawa, Toyohashi (JP); Daisuke Makino, Ichinomiya (JP); Hiroo Imamura, Okazaki (JP); Fumihiko Sato, Susono (JP); Katsuya Hirai, Susono (JP)

(73) Assignees: Denso Corporation, (JP); Nippon Soken, Inc., (JP)

( * ) Notice: Subject to any disclaimer, the term of this patent is extended or adjusted under 35 U.S.C. 154(b) by 0 days.

(21) Appl. No.: 10/686,773

(22) Filed: Oct. 17, 2003

(65) Prior Publication Data
US 2004/0129069 A1    Jul. 8, 2004

(30) Foreign Application Priority Data
Oct. 17, 2002  (JP)  ............................. 2002-303425
Aug. 6, 2003   (JP)  ............................. 2003-287507

(51) Int. Cl.
*G01N 27/407* (2006.01)

(52) U.S. Cl. .................. 73/23.32; 73/23.31; 73/31.05; 204/424

(58) Field of Classification Search ............... 73/31.05, 73/23.31, 23.32; 204/424, 425, 426, 427, 204/428, 429
See application file for complete search history.

(56) References Cited

U.S. PATENT DOCUMENTS

| | | | | |
|---|---|---|---|---|
| 4,683,049 A * | 7/1987 | Nakajima et al. | ........... | 204/428 |
| 6,214,208 B1 * | 4/2001 | Ando et al. | .................. | 205/781 |
| 6,279,376 B1 * | 8/2001 | Yamada et al. | .............. | 73/23.2 |
| 6,327,891 B1 * | 12/2001 | Noda et al. | ................ | 73/31.05 |
| 6,346,179 B1 * | 2/2002 | Makino et al. | ............. | 204/428 |
| 6,688,157 B1 * | 2/2004 | Yamada et al. | .............. | 73/23.2 |
| 6,739,177 B1 * | 5/2004 | Sato et al. | ................. | 73/23.31 |
| 6,780,298 B1 * | 8/2004 | Nakamura et al. | .......... | 204/428 |

FOREIGN PATENT DOCUMENTS

| | | | |
|---|---|---|---|
| JP | 10-123089 | | 5/1998 |
| JP | 2000171430 A | * | 6/2000 |
| JP | 2001-108650 | | 4/2001 |

\* cited by examiner

*Primary Examiner*—Michael Cygan
(74) *Attorney, Agent, or Firm*—Nixon & Vanderhye PC

(57) ABSTRACT

An air-fuel ratio sensor includes a sensor element inserted through a cylindrical housing for detecting an air-fuel ratio in an atmosphere of unburnt gas, and a measured gas side cover disposed on an end of the cylindrical housing so as to cover the sensor element and defining an inside chamber for storing therein a gas to be measured. The cover has a nested structure composed of a plurality of cup-shaped cover members disposed one inside another, each cover member having a gas inlet hole formed in a side wall thereof and a bottom hole formed in a bottom wall thereof. The gas inlet hole of an innermost one of the plural cover members that directly faces the sensor element is offset from an air-fuel ratio detecting portion of the sensor element toward the housing in an axial direction of the sensor.

20 Claims, 17 Drawing Sheets

AIR-FUEL RATIO SENSOR

BACKGROUND OF THE INVENTION

1. Field of the Invention

The present invention relates to an air-fuel ratio sensor for use in an atmosphere of unburnt gas.

2. Description of the Related Art

Air-fuel ratio sensors for detecting an air-fuel ratio in an atmosphere of unburnt gas from the amount of oxygen after reaction of fuel vapor with oxygen are known heretofore. One such known air-fuel ratio sensor includes, as shown here in FIG. 25, a cylindrical housing 10' and an air-fuel ratio sensor element 3' inserted through the housing 10' and capable of detecting an air-fuel ratio of an unburnt gas atmosphere.

The known air-fuel ratio sensor 9 also has an atmospheric side cover 12' disposed on a rear end of the housing 10' and defining an inside chamber for storing atmospheric air, and a measured gas side cover 2' disposed on a front end of the housing 10' so as to cover the air-fuel ratio sensor element 3' and defining an inside chamber for storing a gas to be measured.

The measured gas side cover 2' has a nested structure composed of a plurality cup-shaped cover members 21', 22' disposed one inside another. Each of the cover members 21', 22' has a gas inlet hole 210', 220' formed in a side wall thereof for introducing the gas to be measured, and a bottom hole 219', 229' formed in a bottom wall thereof.

An air-fuel ratio sensor element used for the air-fuel ratio sensor has the same structure as widely known sensor elements used for detecting an oxygen concentration. The air-fuel ratio sensor element is comprised of a solid electrolyte of plate-like or cup-shaped configuration and a pair of electrodes provided on surfaces of the solid electrolytic body. One electrode that is designed for contact with the measured gas has on its surface a diffusion resistance layer. Typical examples of such air-fuel ratio sensor element are disclosed in Japanese Patent Laid-open Publications (JP-A) Nos. 10-123089 and 2001-108650.

Apart from applications in which the air-fuel ratio sensor is used in an atmosphere of burnt gas, such as exhaust gas from an internal combustion engine that is substantially free from flammable or combustible gas especially fuel vapor and the like, an application in which the air-fuel ratio sensor is used in an atmosphere of unburnt gas, such as fuel vapor containing a great quantity of combustible gas, may encounter a problem as discussed below.

When the air-fuel ratio sensor is exposed to an unburnt gas atmosphere that contains large amounts of fuel vapor such as butane, reaction between butane and oxygen on a surface of the sensor element is insufficient so that oxygen to be reacted remains un-reacted and is allowed to reach the electrode. Furthermore, because oxygen has a higher diffusivity than the fuel vapor such as butane with respect to the diffusion resistance layer, the vicinity of the electrode of the air-fuel ratio sensor apparently becomes oxygen-enriched as compared to oxygen concentrations achieved when unburnt gas and oxygen in the measured gas react fully. Consequently, the output from the air-fuel ratio sensor may cause a lean shift, failing to achieve a correct air-fuel ratio measurement.

With the foregoing problem associated with the prior art devices in view, an object of the present invention is to provide an air-fuel ratio sensor which is capable of measuring an air-fuel ratio in an unburnt gas atmosphere with accuracy.

SUMMARY OF THE INVENTION

To achieve the foregoing object, the present invention in one aspect provides an air-fuel ratio sensor comprising a cylindrical housing having a first end and an opposite second end, an air-fuel ratio sensor element inserted through the cylindrical housing and capable of detecting an air-fuel ratio in an atmosphere of unburnt gas, the sensor element having a detecting portion for performing detection of the air-fuel ratio, an atmospheric side cover disposed on the first end of the cylindrical housing and defining an inside chamber for storing therein atmospheric air, and a measured gas side cover disposed on the second end of the cylindrical housing so as to cover the air-fuel ratio sensor element and defining an inside chamber for storing therein a gas to be measured. The measured gas side cover has a nested structure composed of a plurality of cup-shaped cover members disposed one inside another, each of the cup-shaped cover members having a gas inlet hole formed in a side wall thereof for introducing the measured gas into the inside chamber of the measured gas side cover, and a bottom hole formed in a bottom wall thereof. The gas inlet hole of an innermost one of the plurality of cover members that directly faces the air-fuel ratio sensor element is offset from the detecting portion of the air-fuel ratio sensor element toward the housing in an axial direction of the air-fuel ratio sensor.

Since the gas inlet hole of the innermost cover member is offset from the detecting portion of the air-fuel ratio sensor element toward the housing, a combustible gas such as fuel vapor contained in the measured gas is burn away when the measured gas flows or travels over a distance between the gas inlet hole and the detecting portion of the air-fuel ratio sensor element.

Conversely, if the gas inlet hole is disposed in confronting relation to the air-fuel ratio detecting portion, the measured gas may reach the detecting portion with combustible gas left unburnt in the measured gas. Under such condition, reaction between the combustible gas and oxygen becomes insufficient as previously described with respect to the conventional sensor. Additionally, since oxygen has higher diffusivity than the combustible gas, the electrodes of the air-fuel ratio sensor element detect an air-fuel ratio based on the measured gas made in an oxygen-enriched condition. Consequently, the output of the air-fuel ratio sensor causes a lean shift, failing to achieve an accurate measurement of the air-fuel ratio.

In an alternative arrangement in which the gas inlet hole is offset from the air-fuel ratio detecting portion in a direction away from the housing, the measured gas may flow toward a front end of the sensor without contacting the detecting portion. This arrangement cannot perform detection of a gas concentration with accuracy.

In one preferred form of the invention, the cylindrical housing has an end face facing the inside chamber of the measured gas side cover at the second end of the housing, and the detecting portion of the air-fuel ratio sensor element is spaced from the end face of the housing by a distance in the axial direction of the sensor. The gas inlet hole of the innermost cover member has a center located offset from a midpoint of the distance toward the end face of the housing in the axial direction of the sensor.

With this arrangement, the measured gas introduced in the measured gas side cover is allowed to reach the detecting portion of the air-fuel ratio sensor element only after a travel over a sufficiently long distance. During the travel, combustible gas contained in the unburnt gas is burnt away with the result that the detecting portion of the air-fuel ratio sensor element is prevented from becoming oxygen-enriched more than the original condition of the measured gas.

In the case where the center of the gas inlet hole is not located closer to the housing than the midpoint of the foregoing distance, the measured gas is allowed to travel over a relatively short distance. Thus, full combustion or burning of the combustible gas is difficult to achieve.

The position of the end face of housing is determined by a plane containing a surface of the housing at the second end thereof where the housing is in contact with the measured gas. The position of the one end of the air-fuel ratio detecting portion is determined by a plane containing an end of the detecting portion which is closest to the rear end of the air-fuel ratio sensor among those parts contributing to the detection of air-fuel ratio. The axial direction of the air-fuel ratio sensor is a direction parallel to the axis of the cylindrical air-fuel ratio sensor.

It is preferable that the total area of the gas inlet hole of each cover member has a minimum value in the range of 0.3 to 12 mm$^2$. Each of the plural cover members may have one or more gas inlet holes. The total area of the gas inlet hole or holes of one cover member is compared with the total area of the gas inlet hole or holes of another cover member so as to determine a cover member which is smallest in the total area of the gas inlet hole or holes. The total area of the gas inlet hole or holes of the thus determined cover member should preferably take a value in the range as specified above. This arrangement improves the detection accuracy of the air-fuel ratio sensor.

If the total area is less than 0.3 mm$^2$, smooth entry of the measured gas into the measured gas side cover cannot be achieved with the result that the response of the sensor is deteriorated. On the other hand, if the total area is greater than 12 mm$^2$, the amount of introduced gas increases with result that the absolute amount of combustible gas in the unburnt gas increases to the extent that part of the combustible gas remains unburnt.

It is also preferable that the total area of the bottom hole of each cover member has a minimum value in the range of 0.3 to 12 mm$^2$. Each of the plural cover members may have one or more bottom holes. The total area of the bottom hole or holes of one cover member is compared with the total area of the bottom hole or holes of another cover member so as to determine a cover member which is smallest in the total area of the bottom hole or holes. The total area of the bottom hole or holes of the thus determined cover member should preferably take a value in the range as specified above. This arrangement improves the detection accuracy of the air-fuel ratio sensor.

The bottom hole or holes have the function of an gas outlet hole from which the measured gas introduced through the gas inlet hole or holes into the cover member flows out to the outside of the sensor. Thus, the gas flow rate of the measured gas within the measured gas side cover is controlled depending on the total are of the bottom hole or holes. Accordingly, if the total area is less than 0.3 mm$^2$, smooth displacement of the measured gas cannot be achieved with the result that the response of the sensor is deteriorated. On the other hand, if the total area is greater than 12 mm$^2$, the amount of displacement of the measured gas increases with result that the absolute amount of combustible gas in the unburnt gas increases to the extent that part of the combustible gas remains unburnt.

The minimum total area in the range of 0.3 to 12 mm$^2$ is not required for both of the gas inlet hole and the bottom hole but may be satisfied by either one of these holes.

The air-fuel ratio sensor may further include a partition structure for blocking flow communication of the measured gas between the gas inlet hole of each cover member and the bottom hole of each cover member. In the course of a flow toward the inside of the measured gas side cover, the measured gas moves into each cover member from the gas inlet hole formed in the same cover member and goes out of the cover member from the bottom hole formed therein. Accordingly, given that the outermost cover member and another cover member located immediately inside the outermost cover member define therebetween an annular space, the measured gas introduced from the gas inlet hole of the outermost cover member into the annular space would flow outside the measured gas side cover from the bottom hole of the outermost cover member without moving toward the gas inlet hole formed in another cover member. In this instance, because only an insufficient amount of measured gas can reach the air-fuel ratio sensor element, accurate air-fuel ratio detection is difficult to achieve. By providing the partition structure inside the measured gas side cover, a flow or stream of measured gas advancing from the gas inlet hole directly to the bottom hole in each cover member is blocked and the measured gas is guided into the gas inlet hole of an inner cover member to thereby ensure an accurate air-fuel ratio detection.

To form part of the partition structure, the outer cover member is disposed outside the inner cover member (innermost cover member) with a bottom wall thereof held in close contact with a bottom wall of the inner cover member, and an explosionproof cover disposed outside the outer cover member with a bottom wall thereof separated from the bottom wall of the outer cover member. The partition structure includes the bottom walls of the inner and outer cover members held in close contact with each other, and a partition plate hermetically fitted in the explosionproof cover member and held in close contact with the bottom wall of the explosionproof cover member. The partition plate may have an outer peripheral portion extending obliquely from the bottom wall of the outer cover member toward the bottom wall of the explosionproof cover member.

Alternatively, the partition structure may include the bottom walls of the inner and outer cover members held in close contact with each other, and a ring-shaped partition plate hermetically fitted in an annular space defined between the explosionproof cover member and the outer cover member and located adjacent to the bottom wall of the outer cover member. As a further alternative, the partition structure may include the bottom walls of the inner and outer cover members held in close contact with each other, and a truncated hollow cone hermetically fitted in an annular space defined between the explosionproof cover member and the outer cover member and having a small diameter end engaged with a side wall the outer cover adjacent to the bottom wall of the outer cover member and an large diameter end engaged with a side wall of the explosionproof cover member adjacent to the bottom wall of the explosionproof cover member.

Alternatively, the partition structure may include the bottom walls of the inner and outer cover members held in close contact with each other, and a part of a side wall of the explosionproof cover member being constricted in a radial inward direction so such that the constricted part of the side wall is in close contact with the bottom wall of the outer cover member. As a further alternative, the partition structure may includes bottom walls of the inner, outer and explosionproof cover members that are held in close contact with each other.

In one preferred form of the invention, the plurality of cover members include an outer cover member disposed immediately outside the innermost cover member, and the gas inlet hole of the outer cover member is offset from the detecting portion of the air-fuel ratio sensor element in a direction away from the housing.

In another aspect the invention provides an air-fuel ratio sensor comprising an air-fuel ratio sensor element capable of detecting an air-fuel ratio in an atmosphere of unburnt gas and having an air-fuel ratio detecting portion for performing detection of the air-fuel ratio, and a heater for keeping the temperature of the air-fuel ratio detecting portion of the sensor element above 800° C. during measurement of the air-fuel ratio.

Since the air-fuel ration detection portion is kept at a sufficiently high temperature, combustible gas in the measured gas rapidly burns away upon arrival at the detecting portion. This prevents the measured gas in the vicinity of the detecting portion from becoming oxygen-enriched more than the original state.

At temperatures below 800° C., the combustible gas is uneasy to combust or require time for burning and, hence, the detecting portion of the sensor element is apparently subject to oxygen-enriched condition. The temperature of the detecting portion should preferably be below 1000° C. Temperatures higher than 1000° C. might exceed a heat resistance limit of the air-fuel ratio sensor element.

According to a further aspect of the present invention, there is provided an air-fuel ratio sensor comprising a cylindrical housing having a first end and an opposite second end, an air-fuel ratio sensor element inserted through the cylindrical housing and capable of detecting an air-fuel ratio in an atmosphere of unburnt gas, the sensor element having a detecting portion for performing detection of the air-fuel ratio, an atmospheric side cover disposed on the first end of the cylindrical housing and defining an inside chamber for storing therein atmospheric air, and a measured gas side cover disposed on the second end of the cylindrical housing so as to cover the air-fuel ratio sensor element and defining an inside chamber for storing therein a gas to be measured. The measured gas side cover has a nested structure composed of a plurality of cup-shaped cover members disposed one inside another, each of the cup-shaped cover members having a gas inlet hole formed in a side wall thereof for introducing the measured gas into the inside chamber of the measured gas side cover, and a bottom hole formed in a bottom wall thereof A portion of the air-fuel ratio sensor element that is disposed in face to face with the gas inlet hole of an innermost cover member of the plurality of cover members has a temperature made higher than a temperature of the detecting portion of the air-fuel ratio sensor element during measurement of the air-fuel ratio.

Since that portion of the sensor element which directly faces the gas inlet hole of the innermost cover member has a temperature made higher than a temperature of the detecting portion of the sensor element during air-fuel ratio measurement, the measured gas introduced from the gas inlet hole of the innermost cover member is heated upon contact with the sensor element portion and combustible gas is rapidly burnt away. The detecting portion of the sensor element is thus prevented from becoming oxygen-enriched more than the original condition of the measured gas.

In still another aspect the present invention provides an air-fuel ratio sensor comprising a cylindrical housing having a first end and an opposite second end, an air-fuel ratio sensor element inserted through the cylindrical housing and capable of detecting an air-fuel ratio in an atmosphere of unburnt gas, an atmospheric side cover disposed on the first end of the cylindrical housing and defining an inside chamber for storing therein atmospheric air, and a measured gas side cover disposed on the second end of the cylindrical housing so as to cover the air-fuel ratio sensor element and defining an inside chamber for storing therein a gas to be measured. The measured gas side cover has a nested structure composed of a plurality of cup-shaped cover members disposed one inside another, and each of the cup-shaped cover members has a catalytic layer disposed over a surface thereof. The catalytic layer is preferably made of a catalytic material such as Pt or Rh.

The catalytic layer provided on each of the cover members promotes burning of combustible gas that is contained in the measured gas. Accordingly, before the measured gas reaches the sensor element, the combustible gas is fully burnt away. An air-fuel ratio detecting portion of the sensor element is therefore prevented from becoming oxygen-enriched more than the original condition of the measured gas.

According to a further aspect of the present invention, there is provided an air-fuel ratio sensor comprising an air-fuel ratio sensor element capable of detecting an air-fuel ratio in an atmosphere of unburnt gas, the sensor element having a trap layer of porous ceramics disposed over a surface thereof, the trap layer having a thickness not less than 10 $\mu$m.

The trap layer is relatively thick such as not less than 10 $\mu$m and hence is capable of delaying arrival of the measured gas at electrodes on the sensor element. Combustible gas contained in the measured gas burns away as the measured gas passes through the porous trap layer so that the measured gas when arrived at the electrodes is substantially free from combustible gas. An air-fuel ration detecting portion of the sensor element is therefore prevented from becoming oxygen-enriched more than the original condition of the measured gas. The thickness of the trap layer is preferably not greater than 100 $\mu$m from the viewpoint of good response performance of the sensor element. The trap layer may be formed from a porous ceramics layer having the function of trapping toxic substances.

The air-fuel ratio sensor element may be s a cup-shaped sensor element or a laminated type sensor element. In either type of sensor element, the same effect can be attained. In many cases, the cup-shaped sensor element is used together with a separate ceramics heater adapted to be inserted in an inside chamber of the cup-shaped sensor element. On the other hand, the laminated type sensor element in many cases is used together with a ceramics heater adapted to be laminated with the laminated sensor element.

The air-fuel ratio detecting portion of the sensor element is a portion where a solid electrolyte and an outer electrode are joined together. The detecting portion has an annular shape as it is in the cup-shaped sensor element and a quadrangular or elliptical shape as it is in the laminated type sensor element.

In case where the air-fuel ratio sensor element is a laminated type sensor element, the cover members of the measured gas side cover preferably have a quadrangular shape in cross section. This arrangement can reduce the inside volume of the measured gas side cover, which will promote burning of a combustible gas in a short time.

The air-fuel sensors according to the invention are preferably disposed in a surge tank for measuring an air-fuel ratio in an atmosphere of evaporated gas. As an alternative, the air-fuel ratio sensors may be disposed in an exhaust manifold of a diesel engine for measuring an air-fuel ratio of an atmosphere of engine exhaust gas containing a combustible gas added to on an exhaust side of the engine. In either system, the air-fuel sensors perform detection of an air-fuel ratio in an unburnt gas atmosphere containing large amount of fuel vapor. Such application is particularly suited for the sensors of the invention because various advantageous effects can be attained as will be understood from the description given below.

In the surge tank a fuel is allowed to evaporate and the surge tank is filled with evaporated gas including fuel vapor. To prevent release of the evaporated fuel to the outside, an engine system has been proposed, in which the evaporated gas is fed into an engine combustion chamber through a passage provided separately from a fuel supply passage equipped with an ordinary fuel injector.

In the exhaust manifold of the diesel engine, in order to regenerate a catalytic converter, a fuel is periodically injected into the exhaust manifold to produce a burning reaction for removing by reduction substances collected or adsorbed on the catalytic converter. The air-fuel ratio sensors of the present invention are also useful when applied in the exhaust manifold.

In the air-fuel ratio sensor of the present invention, an outermost one of the plural cover members disposed one inside another to form a measured gas side cover preferably is preferably formed into an explosionproof cover member. By thus providing such explosionproof cover member, it is possible to prevent explosive combustion from occurring when a combustible gas such as fuel vapor contained in an atmosphere of unburnt gas undergoes burning. The explosionproof cover member preferably has a surface temperature below 200° C. and gas inlet holes of a diameter not greater than 0.9 mm so as to achieve a desired flame reducing effect.

The maximum surface temperature 500° C. of the explosionproof cover member is determined in view of an explosion limit of gasoline, namely 257° C. Gasoline is widely used as a fuel of an engine in which the air-fuel ratio sensors of the present invention are preferably used for detecting an air-fuel ratio in an atmosphere of unburnt gas formed in the gasoline engine.

The air-fuel ratio sensor element of the present invention may include an oxygen-ion conductive solid electrolyte of ceramics such as zirconia, a first electrode disposed on one surface of the solid electrolyte for contact with a measured gas, a second electrode disposed on an opposite surface of the solid electrolyte for contact with atmospheric air, and a diffusion resistance layer disposed over the first electrode. The sensor element may further include a trap layer disposed over the diffusion layer for trapping toxic substances contained in the measured gas to thereby protect the diffusion layer and the first electrode.

The air-fuel ratio detecting portion of the sensor element is a portion where the solid electrolyte and the outer electrode are in contact with each other. The detecting portion does not work or produce an output unless it is heated to an activated temperature. Accordingly, in general, a heater is formed integrally with or incorporated in the sensor element. During air-fuel ratio measuring operation, the detecting portion is heated to a temperature above the activated temperature.

Throughout the description, the term "an atmosphere of unburnt gas" or "unburnt gas atmosphere" is used herein to refer to an atmosphere containing great amount of combustible gas. The air-fuel ratio sensors of the present invention are able to perform measurement an air-fuel ratio in an unburnt gas atmosphere which is in an ignitable or combustible state. A typical example of the unburnt gas is an atmosphere containing great amount of fuel vapor (i.e., evaporated gas) that is formed by evaporation inside a fuel tank.

DETAILED DESCRIPTION OF THE PREFERRED EMBODIMENTS

Figure 1:
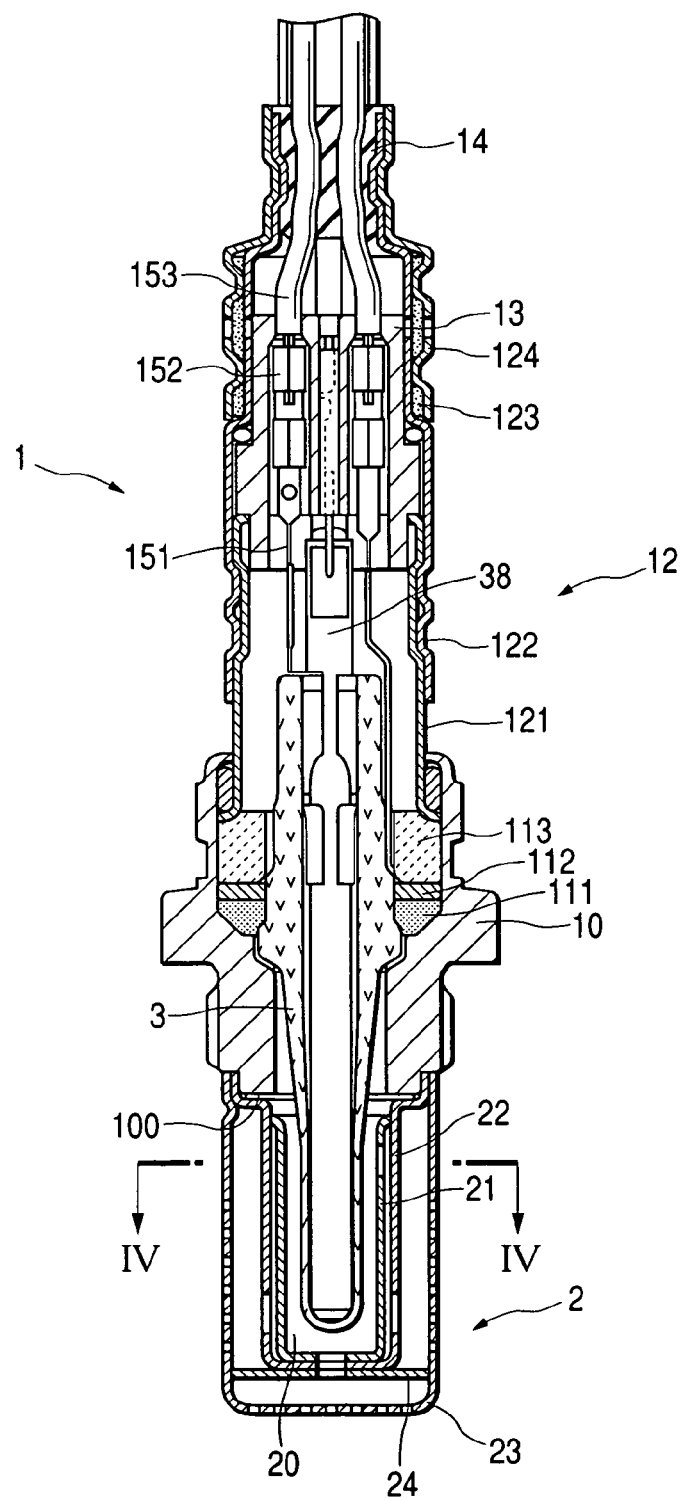
FIG. 1 is a longitudinal cross-sectional view of an air-fuel ratio sensor according to one embodiment of the present invention.

Certain preferred structural embodiments of the present invention will be described in detail herein below, by way of example only, with the reference to the accompanying drawings, in which identical or corresponding parts are denoted by the same reference characters throughout views.

(First Embodiment)

FIGS. 1 through 8 show an air-fuel ratio sensor according to a first embodiment of the present invention. As shown in FIG. 1, the air-fuel ratio sensor 1 is generally cylindrical in configuration and has a front end (lower end in FIG. 1) adapted to be exposed to a gas be measured, and a rear end (upper end in FIG. 1) adapted to be exposed to atmospheric air. The air-fuel ratio sensor 1 generally comprises a cylindrical housing 10, an air-fuel ratio sensor element 3 inserted through the cylindrical housing 10 and capable of detecting an air-fuel ratio in an atmosphere of unburnt gas, an atmospheric side cover 12 disposed on one end (upper end in FIG. 1) of the cylindrical housing 10 and defining an inside chamber for storing atmospheric air, and a measured gas side cover 2 disposed on the other end (lower end in FIG. 1) of the cylindrical housing 10 so as to cover the air-fuel ratio sensor element 3 and defining an inside chamber for storing a gas to be measured. The measured gas side cover 2 has a nested structure composed of a plurality (three in the illustrated embodiment) of cup-shaped or bottomed hollow cylindrical cover members 21, 22, 23 disposed one inside another. As shown in FIG. 1, each of the cup-shaped cover members 21, 22, 23 has at least one gas inlet hole 210, 220, 230 formed in a side wall 211, 221, 231 thereof for introducing the measured gas into the inside chamber of the measured gas side cover 2, and a bottom hole 219, 229, 239 formed in a bottom wall thereof 218, 228, 238.

The gas inlet hole 210 formed in the side wall 211 of an innermost one 21 of the plurality of cover members 21, 22, 23 that directly faces the air-fuel ratio sensor element 3 is offset from an air-fuel ratio detecting portion 39 of the air-fuel ratio sensor element 3 toward the rear end of the air-fuel ratio sensor 1 in an axial direction of the air-fuel ratio sensor 1.

Figure 11:
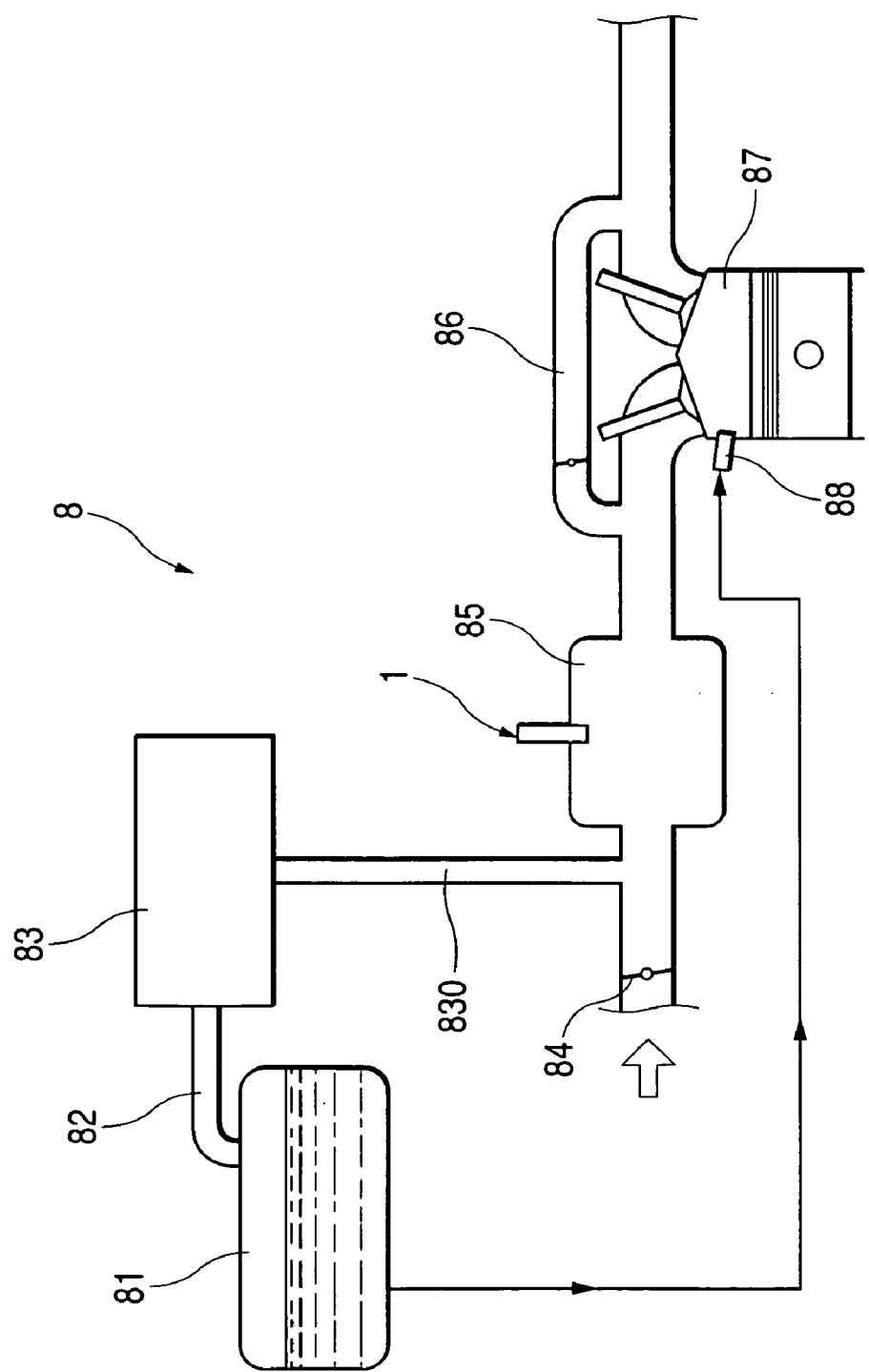
FIG. 11 is a diagrammatical view showing a fuel vapor treatment system in which the air-fuel ratio sensor is incorporated.

The air-fuel ratio sensor 1 in this embodiment is used as being disposed in a surge tank 85 of a fuel vapor processing system 8, as shown in FIG. 11. As shown in this figure, an automotive engine has a combustion chamber 87 into which a fuel such as gasoline supplied from a fuel tank 81 is injected from an injector 88. The fuel tank 81 communicates through a passage 82 with a canister 83 so that fuel vapor inside the fuel tank is fed through the passage 82 into the canister 83 and temporarily absorbed by an and held in absorbing agent such as activated carbon. A gas containing fuel vapor is called evaporated gas.

The canister 83 communicates through a purge passage 830 with an intake passage between a throttle valve 84 and the surge tank 85 so as to purge the fuel vapor of the canister 83 by using depression at engine manifold while the engine is running. The fuel vapor is introduced through the purge passage 830 into the combustion chamber 87 together with an intake air and burns together with the fuel injected from the injector 88. Reference numeral 86 in FIG. 11 denotes an EGR (exhaust gas recirculation) passage.

Turning back to FIG. 1, structural details of the air-fuel ratio sensor 1 will be described.

In air-fuel ratio sensor 1, the air-fuel ratio sensor element 3 is hermetically inserted through the cylindrical housing 10. In an annular space defined between the air-fuel ratio sensor element 3 and a peripheral wall of the housing 10, a powdery seal material 111, an annular seal member 112 and an insulator 113 is disposed so that the internal atmosphere of the air-fuel ratio sensor 1 is separated into a measured gas side and an atmospheric side.

The measured gas side cover 2 is disposed on the lower end of the housing 10 which is located on the front end side of the air-fuel ratio sensor 1. The cover 2 is formed into a multi-tube or nested structure having three cup-shaped cover members 21, 22, 23 disposed one inside another. In this embodiment, the outermost cover member 23 is called an explosionproof cover member, the intermediate cover member 22 is called an outer cover member, and the innermost cover member 21 is called an inner cover member. The inner cover member 21 defines a measured gas chamber 20 in which the air-fuel ratio detecting portion 39 (FIGS. 2 and 3) is disposed for undergoing exposure to a gas to be measured. The measured gas chamber 20 when filled with the gas to be measured forms a measured gas atmosphere.

Figure 2:
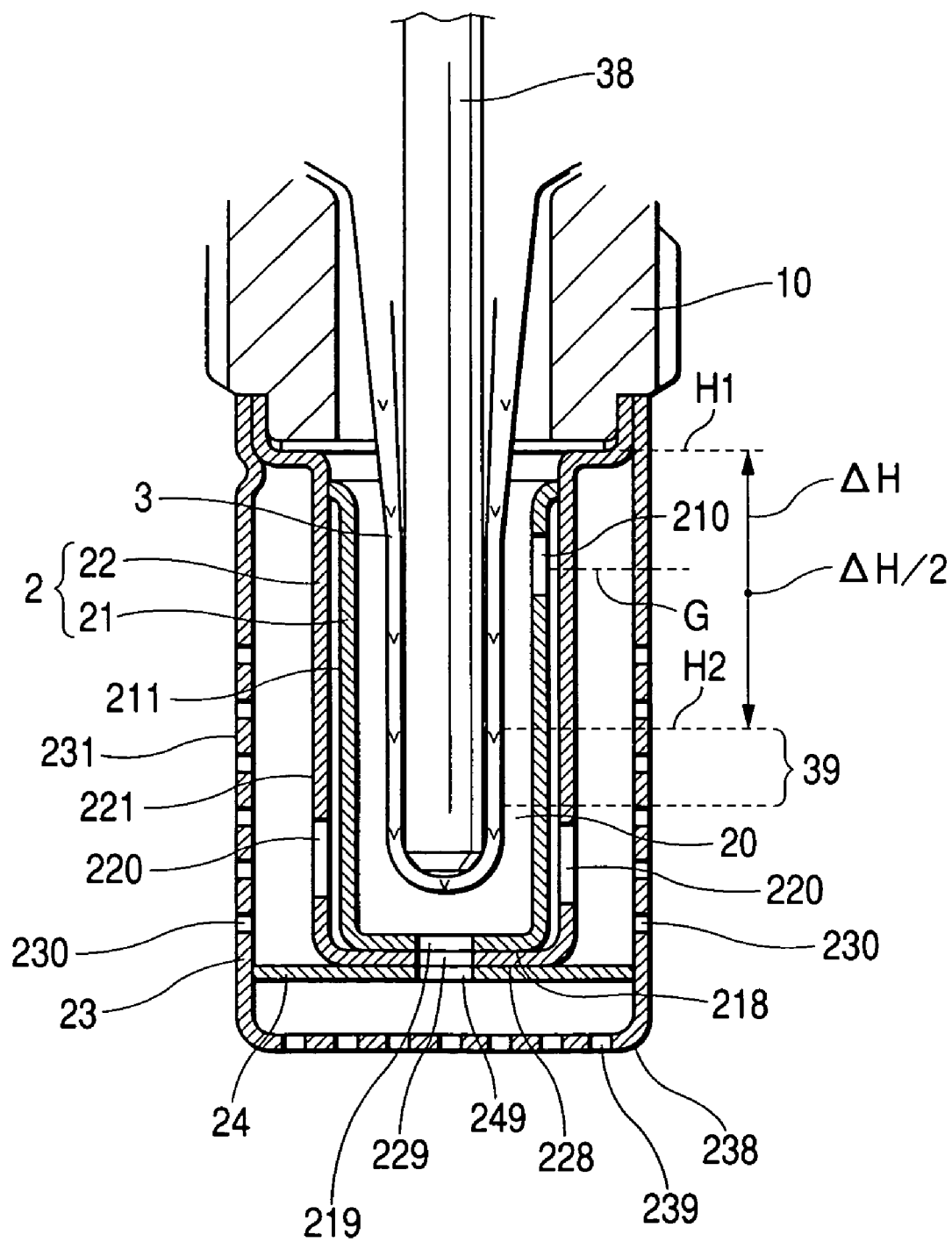
FIG. 2 is a view showing on enlarged scale a portion of the air-fuel ratio sensor including a measured gas side cover and related parts thereof.
Figure 4:
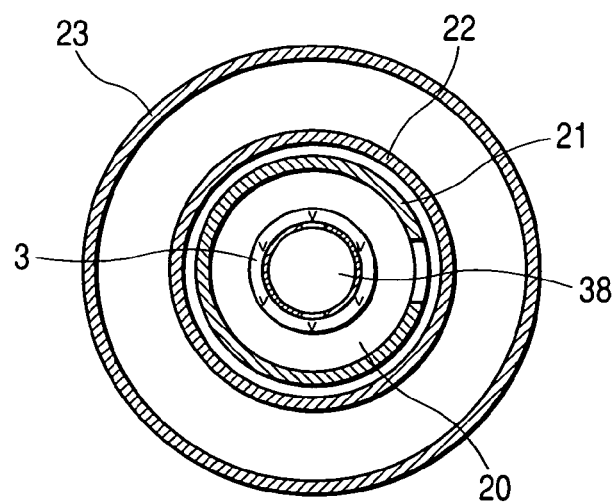
FIG. 4 is a cross-sectional view taken along line IV—IV of FIG. 1.

The cover members 21–23 each have a circular shape in cross section as shown in FIG. 4 and they are shaped into a bottomed cylindrical or cup-shaped configuration as shown in FIG. 2. The bottom walls 218, 228 of the inner and outer cover members 21, 22 are in close contact with each other, while the bottom walls 228, 238 of the outer and explosionproof cover members 22, 23 are separated from each other. There is a partition structure 24 disposed in close contact with the bottom wall 228 of the outer cover member 22 inside the explosion cover member 23. The partition structure 24 has an outside diameter substantially the same as an inside diameter of the explosionproof cover member 23.

The partition structure 24 has a central hole 249. The bottom hole 219 formed in the bottom wall 218 of the inner cover member 21, the bottom hole 229 formed in the bottom wall 228 of the outer cover member 22 and the central hole 249 formed in the partition structure 24 are aligned with each other in the axial direction of the air-fuel ratio sensor 1.

By thus providing the partition structure 24, a measured gas introduced from the gas inlet holes 230 formed in the side wall 231 of the explosionproof cover member 23 is prevented from flowing toward the front end of the air-fuel ratio sensor 1. For the measured gas once flown downward toward the front end side of the air-fuel rate sensor 1 within the measured gas side cover 2, it is difficult to flow back into an upward direction toward the rear end side of the air-fuel ratio sensor 1 and enter the measured gas chamber 20 of the inner cover member 21. This difficulty may cause a delay in response of the air-fuel ratio sensor 1 or lower the detection accuracy of the air-fuel ratio sensor 1. To prevent the measured gas from flowing toward the front end of the air-fuel ratio sensor 1, the partition structure 24 is provided.

As shown in FIG. 1, the atmospheric side cover 12 is disposed on the upper end of the cylindrical housing 10 which is located on the rear end side of the air-fuel ratio sensor 1. The cover 12 is composed of a first cover 121 directly secured by clenching to the housing 10, a second cover 122 connected to an upper end of the first cover 121, and an outside cover 124 connected to an upper end of the second cover 122 a water-repellent filter 123 disposed therebetween.

A rubber bushing 14 is firmly fitted in an upper end of the atmospheric side cover 12. The atmospheric side cover 12 has an internal space in which an insulator 13 is disposed with output terminals 151, connectors 152 and lead wires 153 of the air-fuel ratio sensor element 3 fitted in the insulator 13.

Figure 3:
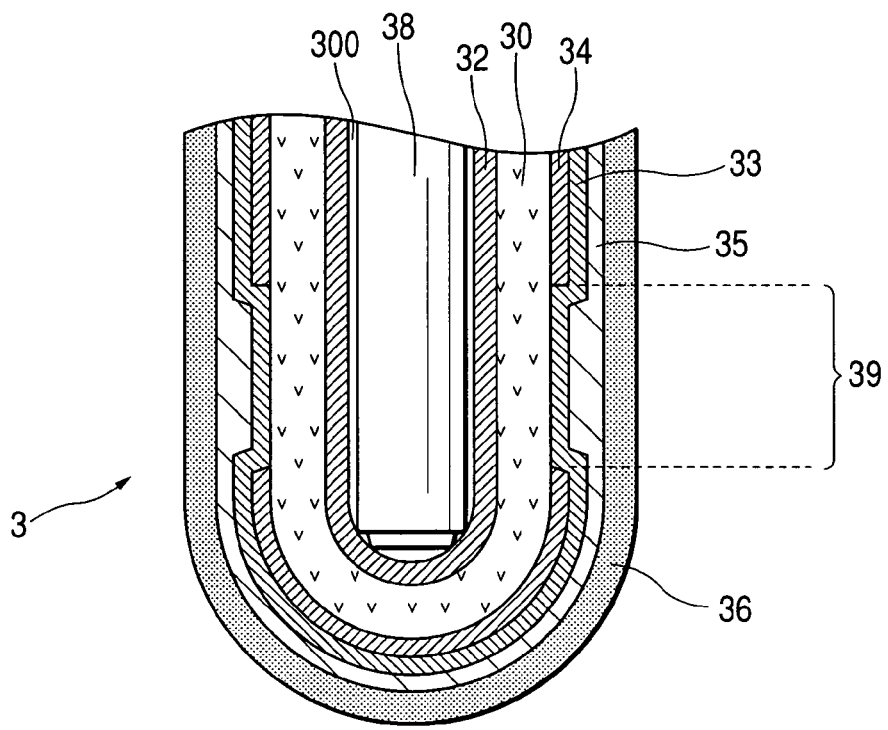
FIG. 3 is a longitudinal cross-sectional view of an air-fuel ratio sensor element.

As shown in FIG. 3, the air-fuel ratio sensor element 3 is a cup-shaped air-fuel ratio sensor element comprised of a bottomed hollow cylindrical or cup-shaped solid electrolyte 30. The sensor element 3 includes inner and outer electrodes 32 and 33 disposed over inside and outside surfaces, respectively, of the cup-shaped solid electrolyte 30, and a diffusion resistance layer 35 of porous ceramics disposed over the outside electrode 33, and a trap layer 36 formed over the diffusion resistance layer 35 for trapping poisonous substances contained in the measured gas.

In order to disable detection by other part than the air-fuel ratio detecting portion 39, an insulating layer 34 is provided between the solid electrolyte 30 and the outer electrode 33. The solid electrolyte 30 defines therein an atmospheric chamber 300 communicating with the atmospheric air held inside the atmospheric side cover 12. A rod-like ceramic heater 38 is inserted in the atmospheric chamber 200.

The measured gas side cover 2 will be described below in greater detail. As previously described, the cover 2 in the first embodiment has a nested structure in which three cover members of configurations shown in FIGS. 4–7, namely, the inner cover member 21, outer cover member 22 and explosionproof cover member 23 are disposed one inside another.

Figure 5A:
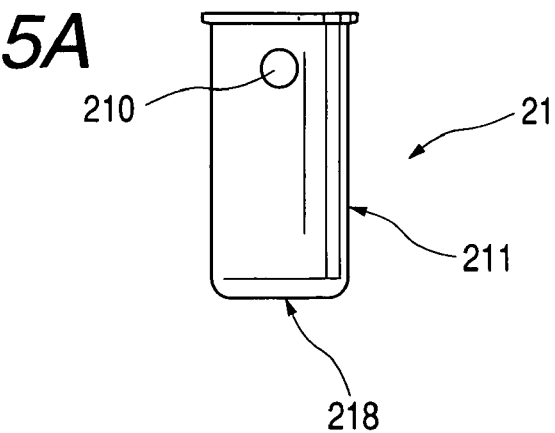
FIG. 5A is a front elevational view of an inner cover member of the measured gas side cover.
Figure 5B:
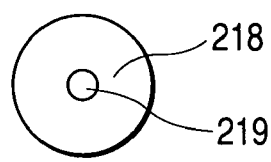
FIG. 5B is a bottom view of the inner cover member.
Figure 8:
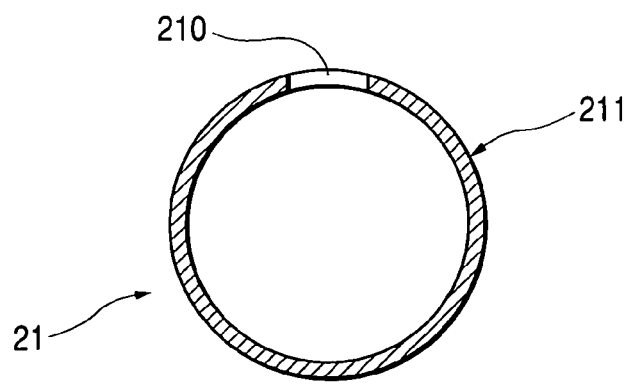
FIG. 8 is a transverse cross-sectional view of the inner cover member showing a gas inlet hole thereof.

As shown in FIGS. 5A, 5B and 8, the inner cover member 21 has a single gas inlet hole 210 formed in the side wall 211 thereof, and a single bottom hole 219 formed in the bottom wall 218 thereof. The single air inlet hole 210 is located close to an upper end (open end) of the cup-shaped inner cover member 21, and the bottom hole 219 is located at the center of the circular bottom wall 218.

Figure 9:
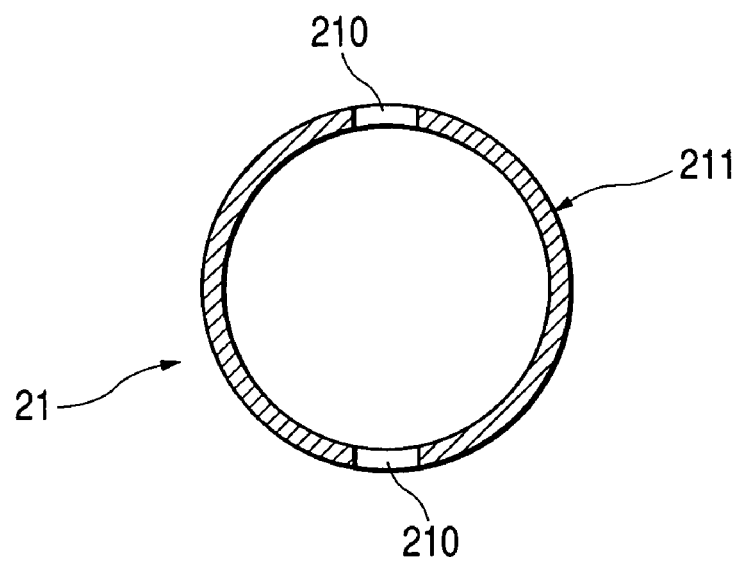
FIG. 9 is a view similar to FIG. 8, but showing an arrangement of gas inlet holes according to a modification of the present invention.
Figure 10:
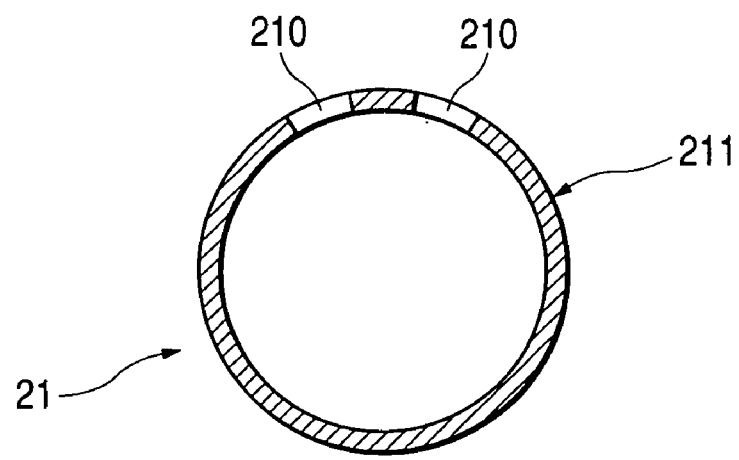
FIG. 10 is a view similar to FIG. 8, but showing an arrangement of gas inlet holes according to another modification of the present invention.

According to the present invention, the inner cover member 21 may be modified to have two gas inlet holes 210, 210 that are formed in diametrically opposite relation, as shown in FIG. 9. FIG. 10 shows another modification in which the inner cover member 21 has two gas inlet holes 210, 210 that are disposed in close juxtaposition at one side of the side wall 211 of inner cover member 21.

Figure 6A:
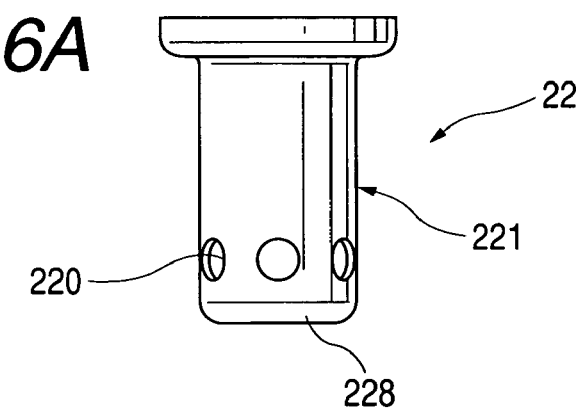
FIG. 6A is a front elevational view of an outer cover member of the measured gas side cover.
Figure 6B:
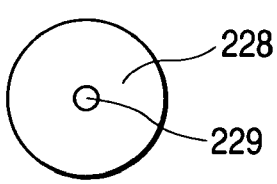
FIG. 6B is a bottom view of the outer cover member.

As shown in FIGS. 6A and 6B, the outer cover member 22 has six gas inlet holes 220 formed in the side wall 221 at regular intervals in the circumferential direction of the outer cover member 22 and spaced from the bottom wall 228 by the same distance, and a single bottom hole 229 formed at the center of the circular bottom wall 228.

Figure 7A:
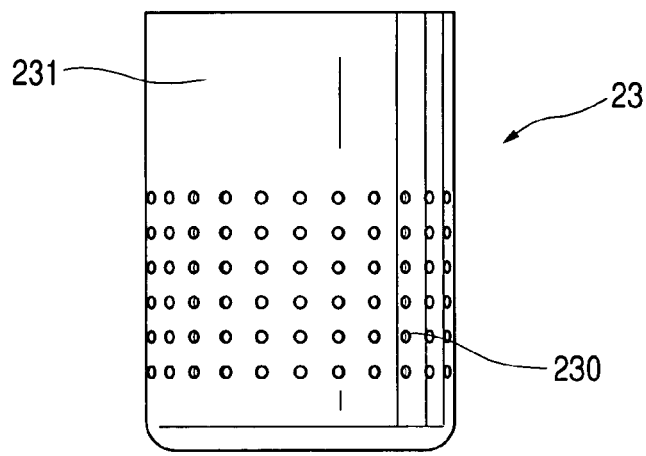
FIG. 7A is a front elevational view of an explosionproof cover member of the measured gas side cover.
Figure 7B:
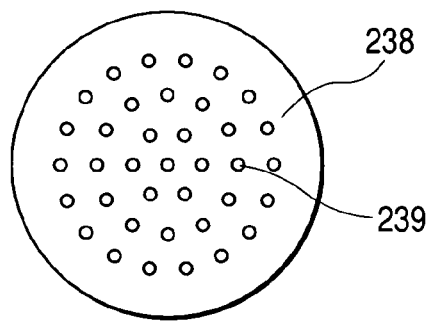
FIG. 7B is a bottom view of the explosionproof cover member.

The explosionproof cover member 23, as shown in FIGS. 7A and 7B, has a total of 168 regularly arranged gas inlet holes 230 formed in the side wall and a total of 37 regularly arranged bottom holes 239 formed in the bottom wall 238. The gas inlet holes 230 and the bottom holes 239 both operate as explosion-proofing holes. The gas inlet holes 230 of the explosionproof cover member 23 provides a first inlet from which a gas to be measured is allowed to enter the inside of the measured gas side cover 2.

Turning back to FIG. 2, the position of the center of the gas inlet hole 210 of the inner cover member 21 is designated by G, the position of a lower end face of the cylindrical housing 10, which faces the inside chamber of the inner cover member 21, is designated by H1, the position of an upper end of the air-fuel ratio detecting portion 39 (which is located on the rear end side of the sensor 1 when viewed from an lower end of the detecting portion 39) is designated by H2, and the distance between H1 and H2 is designated by $\Delta H$. Under such condition, the position of G is offset from a midpoint ($\Delta H/2$) of the distance toward the housing 10. Stated in other words, the center G of the gas inlet hole 210 is located at a position spaced from the end face H1 of the housing 10 in the axial direction of the sensor 1 by a second distance smaller than one-half ($\Delta H/2$) of the first distance $\Delta H$. Reference character G denotes the center of the gas inlet hole 210, which is circular in shape. For a gas inlet hole having non-circular shape, G represents a barycentric position of the non-circular gas inlet hole. The lower end face of housing 10 designated by H1 is defined as a surface where the housing 10 is in contact with the measured gas atmosphere, and the upper end of air-fuel ratio detecting portion 39 designated by H2 is defined as a part of the detecting portion 39 that is closest to the rear end of the air-fuel ratio sensor 1 among the detecting portion 39.

The gas inlet hole 210 has a diameter of 2.5 mm, and the bottom hole 219 has a diameter of 2.0 mm. The gas inlet holes 220 have a diameter of 3.0 mm, and the bottom hole 229 has a diameter of 2.0 mm. The gas inlet holes 230 and the bottom holes 239 both serving as explosion-proofing holes have a diameter of 0.9 mm. Accordingly, the gas inlet hole 210 of the inner cover member 21 has a total area of 4.9 mm$^2$ and the bottom hole 219 has a total area of 3.14 mm$^2$. Similarly, the gas inlet holes 220 of the outer cover member 22 have a total area of 42.4 mm$^2$ and the bottom hole 229 has a total area of 3.14 mm$^2$. The gas inlet holes 230 of the explosionproof cover member 23 have a total area of 106.82 mm$^2$ and bottom holes 239 have a total area of 23.53 mm$^2$.

Performance of the air-fuel ratio sensor 1 of the foregoing construction is measured in a manner as described below.

Figure 25:
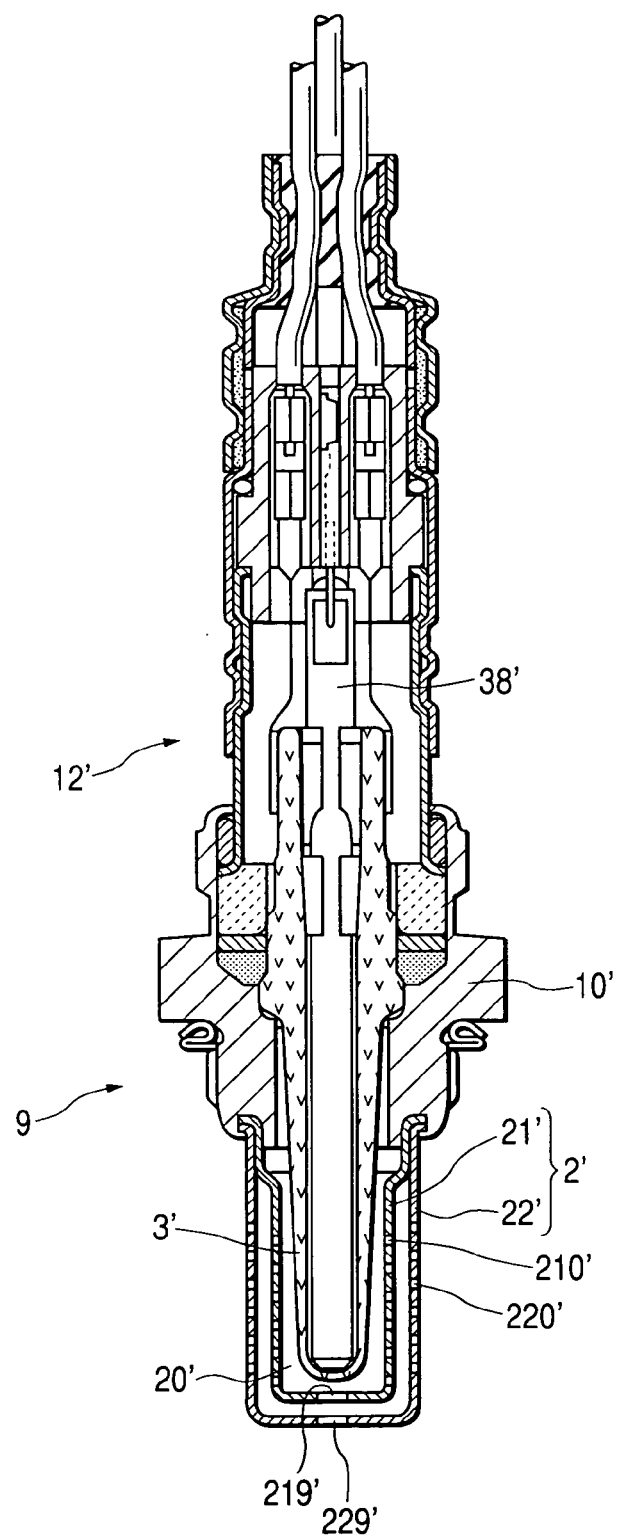
FIG. 25 is a longitudinal cross-sectional view of a conventional air-fuel ratio sensor.

An atmosphere of unburnt gas containing a predetermined quantity of butane is prepared and the output of the air-fuel ratio sensor 1 is measured in the unburnt gas atmosphere. For comparative purposes, a conventional air-fuel ratio sensor formed by setting the same air-fuel ratio sensor element 3 as the present invention in the prior art air-fuel ratio sensor 9 shown in FIG. 25 is measured for its output in the unburnt gas atmosphere. On condition that the output of the air-fuel ratio sensor has a value 1 (one) when the butane concentration is 0 (zero) wt %, a sensor output ratio is calculated for each butane concentration with the results shown in FIG. 12.

Figure 12:
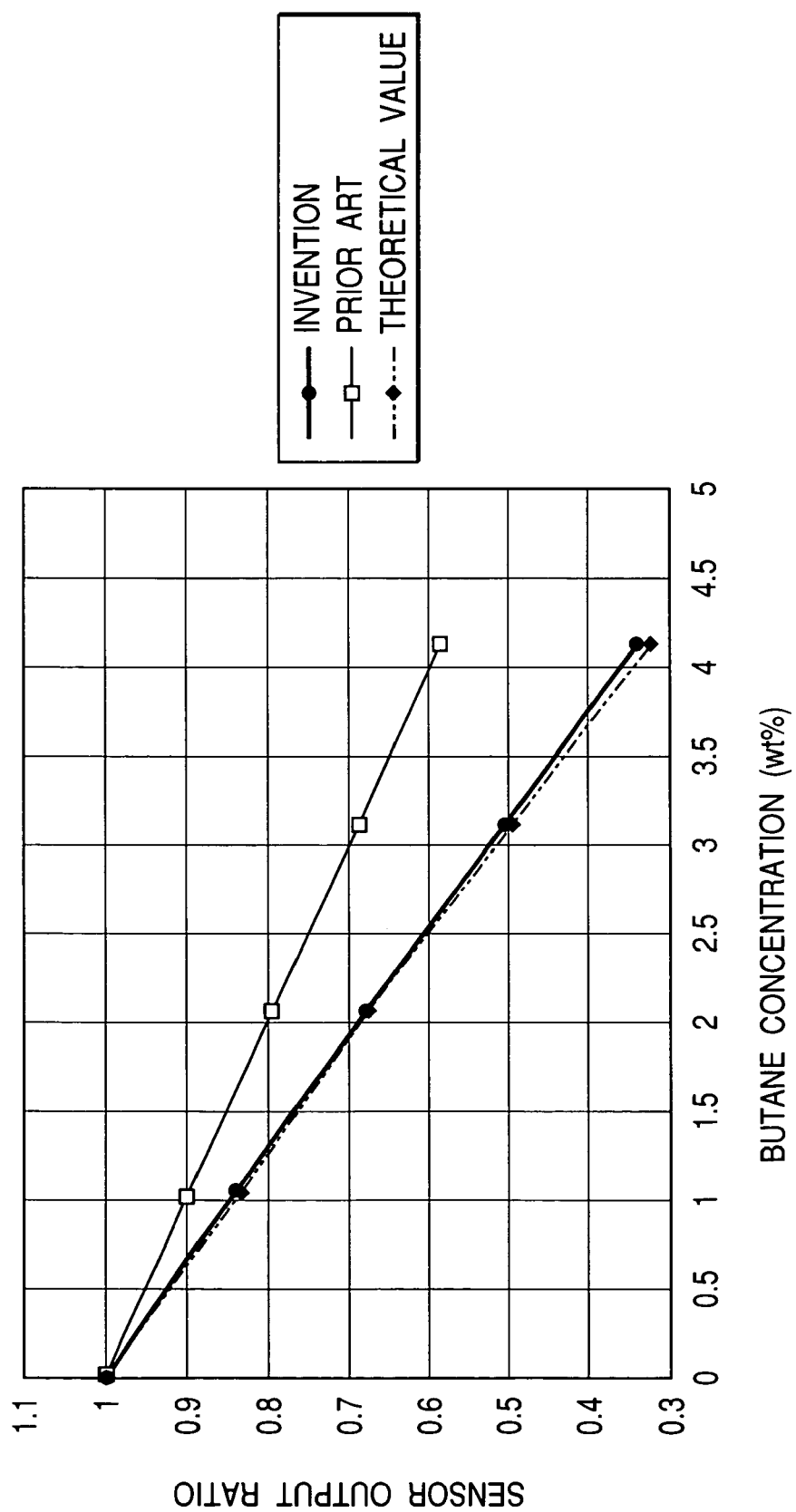
FIG. 12 is a graph showing, for comparative purposes, performance curves of the inventive, conventional and theoretical sensors that are drawn to show the relationship between the sensor output ratio and the butane concentration in a gas to be measured.

As shown in FIG. 12, the sensor output ratio decreases as the butane concentration increases. This is because the oxygen concentration increases with the butane concentration. However, due to insufficient reaction between butane and oxygen, the conventional air-fuel ratio sensor causes an apparent oxygen-enriched condition. As a result, the sensor output ratio of the conventional sensor takes values that, as represented by a thin solid line shown in FIG. 12, are offset from corresponding theoretical values represented by a phantom line shown in the same figure. The amount of offset becomes greater as the butane concentration increases. This means that the output of the conventional sensor involves a great error. On the other hand, the sensor output ratio of the inventive sensor takes values, which, as represented by a thick solid line shown in FIG. 12, are nearly equal to the corresponding theoretical values represented by the phantom line in the same figure. It is evident from FIG. 12 that the air-fuel ratio sensor 1 of the present invention can measure an air-fuel ratio with extremely high accuracy.

Operation of and advantageous effects attained by the air-fuel ratio sensor 1 are as follows. In the air-fuel ratio sensor 1, the gas inlet hole 210 of the inner cover member 21 is located closer to the rear end of the air-fuel ratio sensor 1 than the air-fuel ratio detecting portion 39 does (see FIG. 2). Furthermore, as shown in FIG. 2, when the position of the center of the gas inlet hole 210 of the inner cover member 21 is represented by G, the position of a lower end face of the housing 10 is represented by H1, the position of an upper end of the air-fuel ratio detecting portion 39 (that is located closer to the rear end of the sensor 1 than the lower end of the same detecting portion 39) is represented by H2, and a distance between H1 and H2 is represented by ΔH, the center G of the gas inlet hole 210 is located closer ΔH than the midpoint of the distance ΔH/2 with respect to the rear end of the air-fuel ratio sensor 1.

With this arrangement, a measured gas introduced in the measured gas side cover 2 can reach the detecting portion 39 of the air-fuel ratio sensor element 3 only after a travel over a sufficiently long distance. During such long distance travel, a combustible gas contained in the unburnt gas is fully burnt away with the result that the detecting portion 39 of the air-fuel ratio sensor element 3 is prevented from becoming oxygen-enriched more than the original condition of the measured gas.

Furthermore, among three cover members 21, 22, 23, the inner cover member 21 is smallest in the total area of the gas inlet hole. As for the total area of the bottom hole, the inner cover member 21 is equal to the outer cover member 22. The total area of each bottom hole is smaller than that of the gas inlet hole or holes and is not greater than 12 mm$^2$. In each cover member 21, 22, a flow of measured gas undergoes rate-controlling at either of the gas inlet hole 210, 220 or the bottom hole 219, 229 which has a smaller total area than the other. In case of the air-fuel ratio sensor 1 of the present invention, since the total area of the bottom hole 219, 229 is not greater than 12 mm$^2$, the measured gas is displaced smoothly and unburnt gas does not increase so much, nor does it remain unburnt.

Furthermore, during air-fuel ratio measuring operation, the heater 38 is energized or activated so as to keep the temperature of the air-fuel ratio detecting portion 39 of the sensor element 3 above 800° C.

By thus keeping the air-fuel ration detection portion 39 at a sufficiently high temperature, combustible gas contained in the measured gas is allowed to undergo full combustion or burning upon arrival at the detecting portion 39. This prevents the detecting portion 39 from becoming oxygen-enriched more than the original state of the measured gas.

At temperatures below 800° C., the combustible gas is uneasy to combust or require time for burning and, hence, the detecting portion 39 of the sensor element 3 is apparently subject to oxygen-enriched condition. The temperature of the detecting portion should preferably be below 1000° C. Temperatures higher than 1000° C. might exceed a heat resistance limit of the air-fuel ratio sensor element 3.

It will be appreciated from the foregoing discussion that the air-fuel ratio sensor 1 provided in accordance with the first embodiment of the invention can measure with accuracy an air-fuel ratio in an atmosphere of unburnt gas.

(Second Embodiment)

In this embodiment, the air-fuel ratio sensor 1 shown in FIG. 1 is used with a modification that the ceramic heater 38 inserted in the sensor element 3 as shown in FIGS. 1 and 2 is adjusted to heat the sensor element 3 in such a manner that a part of the sensor element 3 that faces the gas inlet hole 210 formed in the side wall 211 of the inner cover member 21 is higher in temperature than the air-fuel ratio detecting portion 39 of the sensor element 3.

By thus adjusting the heater 38, a measured gas introduced from the gas inlet hole 211 into the measured gas chamber 20 comes into contacted with the heated part of the sensor element 3 whereupon the measured gas is heated and combustible gas contained in the measured gas is rapidly burnt away. Consequently, the detecting portion 39 of the air-fuel ratio sensor element 3 is prevented from becoming oxygen-enriched more than original condition of the measured gas.

(Third Embodiment)

Figure 13:
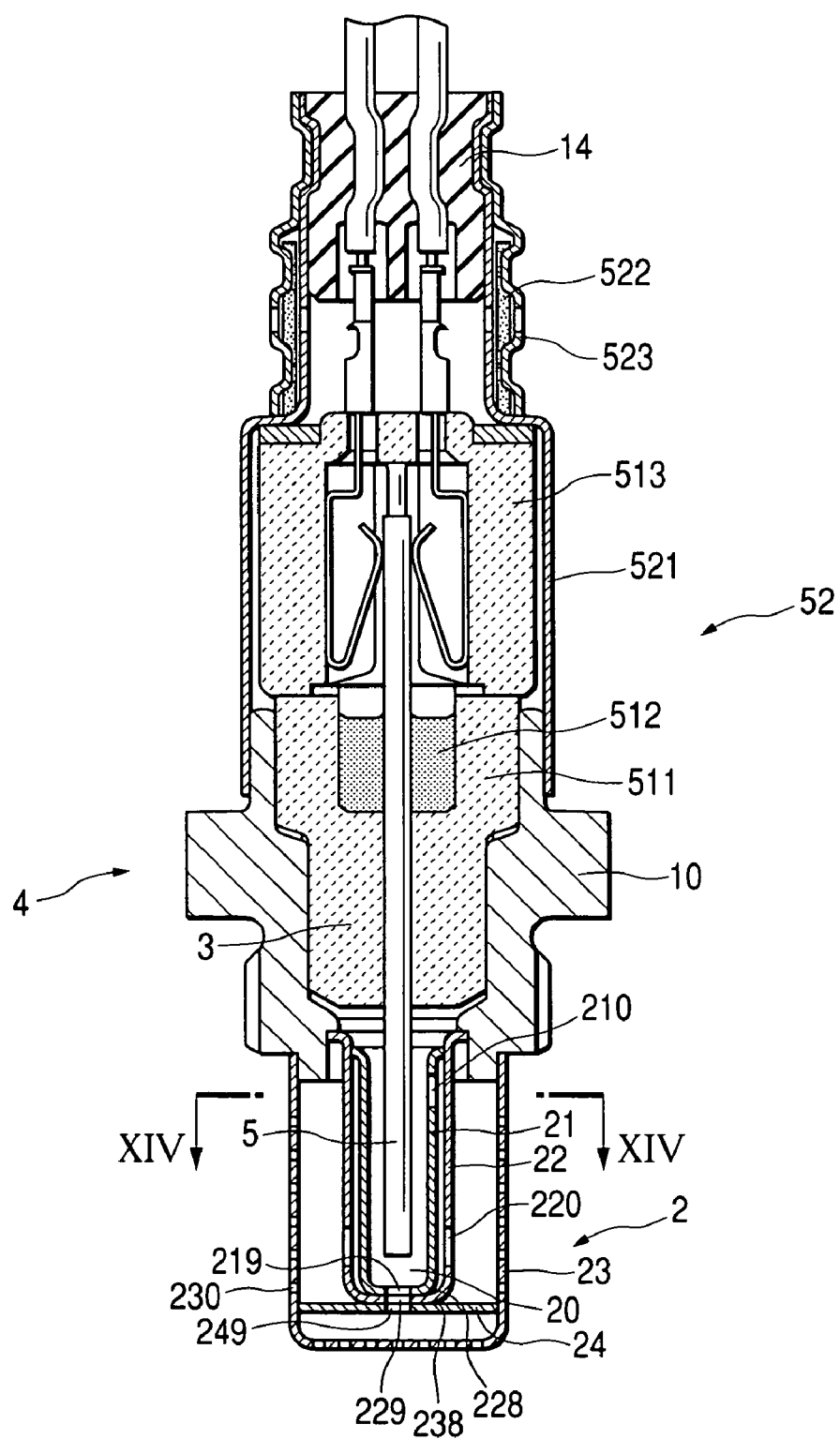
FIG. 13 is a longitudinal cross-sectional view of an air-fuel ratio sensor according to another embodiment of the present invention having a laminated type sensor element.
Figure 14:
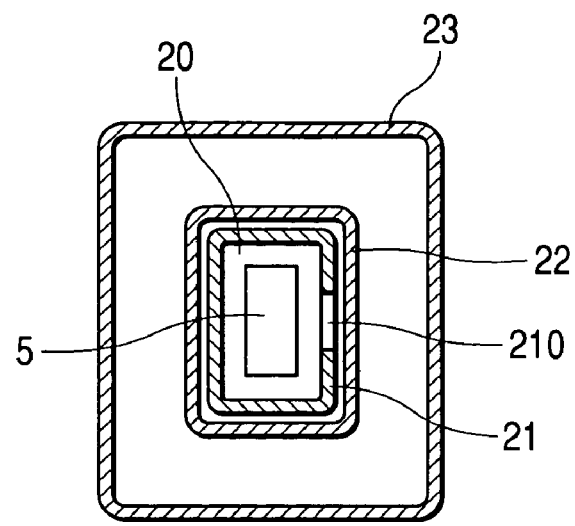
FIG. 14 is a cross-sectional view taken along line XIV—XIV of FIG. 13.

FIG. 13 shows an air-fuel ratio sensor 4 according to a second embodiment of the present invention. The sensor 4 is equipped with a laminated type air-fuel ratio sensor element 5.

More specifically, the air-fuel ratio sensor 4 generally comprises a cylindrical housing 10 and the air-fuel ratio sensor element 5 hermetically inserted through the cylindrical housing 10. The sensor element 5 is inserted through the cylindrical housing 10 with an insulator 511 disposed therebetween. The sensor element 5 and the insulator 511 are sealed together by a seal member 512. Another insulator 513 is disposed on an upper end of the insulator 511 that is located on a rear end side of the sensor 4.

A measured gas side cover 2 is disposed on a lower end of the housing 10 that is located on a front end side of the sensor 4. The cover 2 has a nested structure composed of three cup-shaped cover members 21, 22, 23 disposed one inside another. The innermost cover member is an inner cover member 21, the intermediate cover member is an outer cover member 22, and the outermost cover member is an explosionproof cover member 23. The inner cover member 21 defines therein a measured gas chamber 20 in which an air-fuel ratio detecting portion (not shown) of the sensor element 4 is disposed for undergoing exposure to a measured gas atmosphere formed in the measured gas chamber 20.

An atmospheric side cover 52 is disposed on an upper end of the housing 10 that is located on the rear end side of the air-fuel ratio sensor 4. The cover 52 includes a first cover 521 directly attached to the housing 10, and a second cover 523 mounted on an upper end portion of the first cover 521 with a water-repellent filter 522 disposed therebetween. An upper end of the atmospheric side cover 52 is closed by a rubber bushing 14, and the insulator 513 is disposed in an internal space of the cover 52.

The measured gas side cover 2 of the air-fuel ratio sensor 4 has the same nested structure as the one 2 of the air-fuel ratio sensor 1 of the first embodiment but differs from the cover 2 of the sensor 1 in that the cross-sectional shape of the cover 2 is quadrangle. Other structural details of the air-fuel ratio sensor 4 are the same as those of the foregoing sensor 1 and no further description thereof is needed.

By using the quadrangular cross-sectional shape, it is possible for the measured gas side cover 2 to reduce the cubic capacity thereof to thereby facilitate burning out of combustible components contained in an unburnt gas.

Operation of and advantageous effects attained by the sensor 4 are the same as those of the sensor 1 in the first embodiment.

(Fourth Embodiment)

Figure 15:
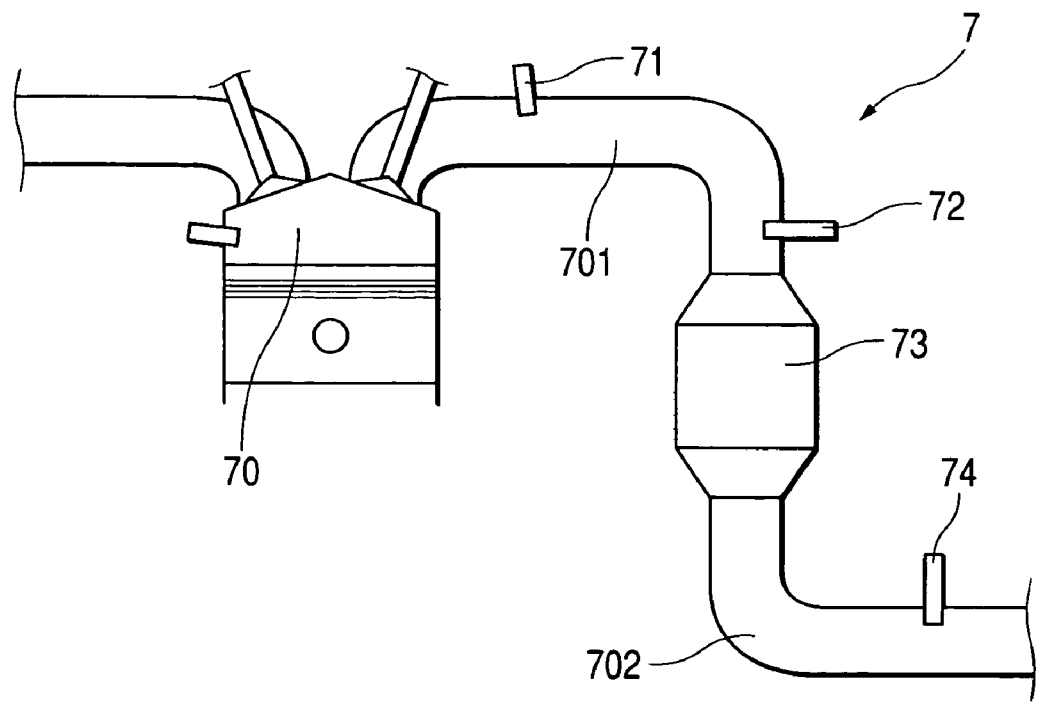
FIG. 15 is a diagrammatical view showing an exhaust system of a diesel engine in which an air-fuel ratio sensor of the present invention may be incorporated.

The air-fuel ratio sensors 1, 4 of the foregoing embodiments may be disposed in an exhaust manifold 701 of a diesel engine, as shown in FIG. 15. In an exhaust system 7 of the diesel engine, exhaust gases from an engine combustion chamber 70 is fed through the exhaust manifold 701 to a catalytic converter 73 from which it passes through an exhaust pipe 702 and is finally discharged to the atmosphere.

The catalytic converter 73 adsorbs air-polluting substances such as NOx to purify the exhaust gases, however, after the lapse of a predetermined time period, adsorption of the air-polluting substances becomes difficult to achieve.

In order to remove the adsorbed air-polluting substances, a fuel injection valve 71 is disposed in the exhaust manifold 701 at a position close to the engine combustion chamber 70 for ejecting a fuel into the exhaust manifold so that the pollutants are removed by reduction from the catalytic converter 73. In this instance, the amount of fuel injection is feedback-controlled by an output signal from a sensor 72 (corresponding to the sensor 1 shown in FIG. 1 or the sensor 4 shown in FIG. 13).

Since an unburnt gas atmosphere may be frequently formed inside the exhaust manifold 701, the sensor 72 used in such unburnt gas atmosphere is preferably formed by any one of the air-fuel ratio sensors of the present invention because it can measure with accuracy an air-fuel ratio in the unburnt gas atmosphere.

Reference numeral 74 shown in FIG. 15 denotes another gas sensor that may be disposed downstream of the catalytic converter 73 in place of the sensor 72. An air-fuel ratio sensor according to the present invention preferably forms the sensor 74.

(Fifth Embodiment)

Figure 16:
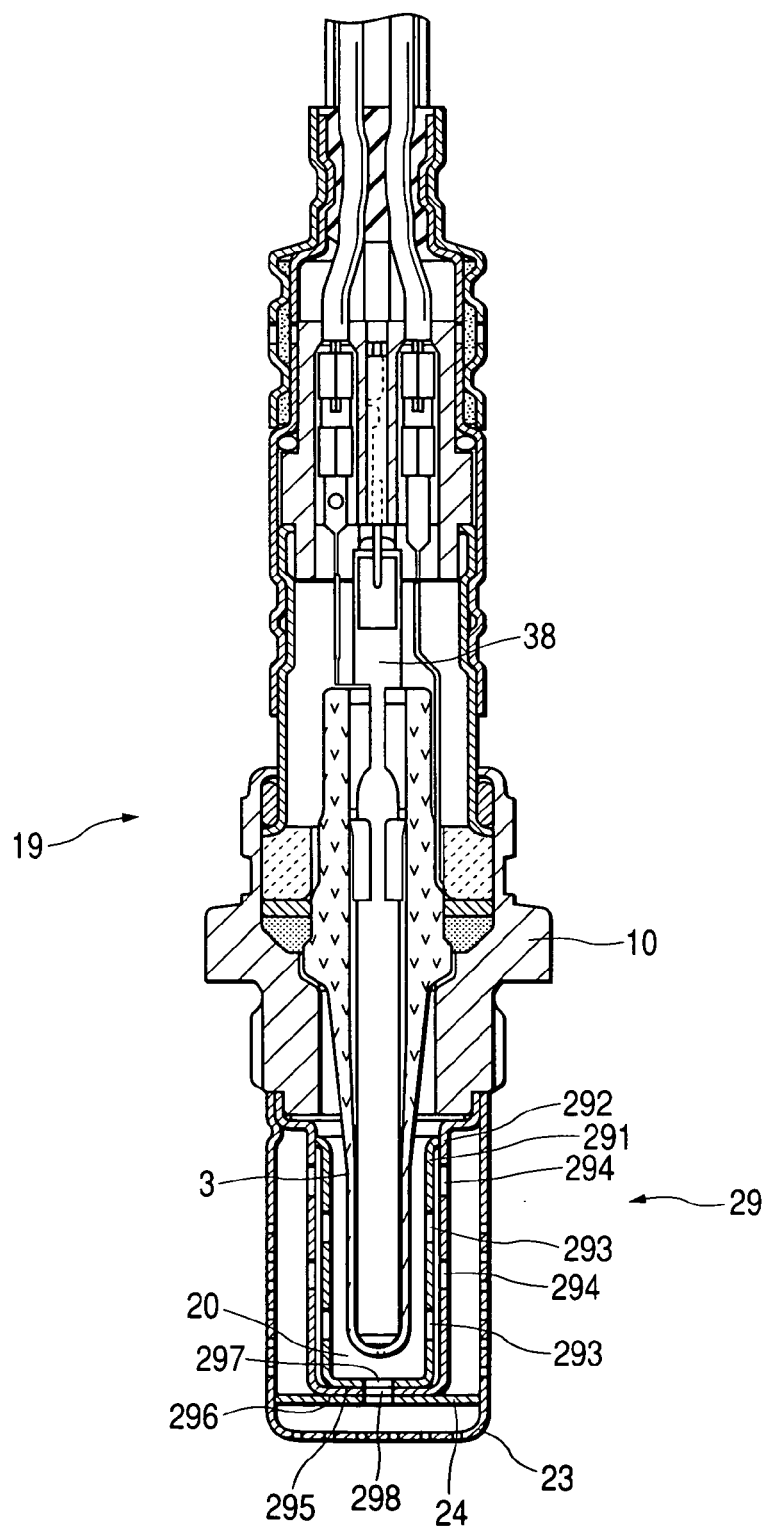
FIG. 16 is a longitudinal cross-sectional view showing an air-fuel ratio sensor according to still another embodiment of the present invention.

FIG. 16 shows an air-fuel ratio sensor 19 having an air-fuel ratio sensor element 3 shown in greater detail in FIG. 16. The air-fuel ratio sensor 19 is structurally similar to the sensor 1 shown in FIG. 1. Inner and outer cover members 291 and 292 of a measured gas side cover 29 have gas inlet holes 293 and 294 formed in staggered relation so that the inlet holes 293 of the inner cover member 291 and the gas inlet holes 294 of the outer cover member 294 are out of alignment in a radial direction of the measured gas side cover 29. The inner and outer cover members 291, 292 have bottom holes 297, 298 formed in the respective bottom walls 295, 296. The arrangement of the inner and outer cover members 291, 292 is the same as conventional gas sensors or air-fuel ratio sensors.

Figure 17:
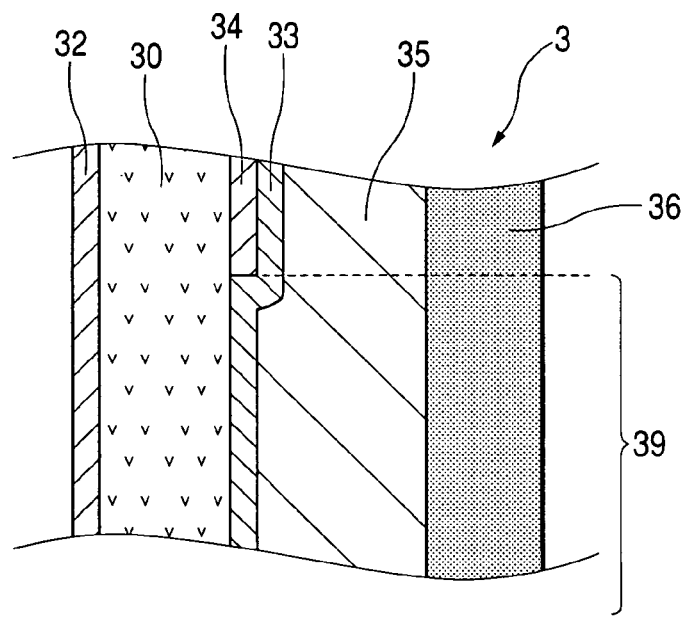
FIG. 17 is a fragmentary cross-sectional view showing part of an air-fuel ratio sensor element incorporated in the sensor shown in FIG. 16.

As shown in FIG. 17, the air-fuel ratio sensor element 3 of the sensor 19 includes a bottomed hollow cylindrical or cup-shaped solid electrolyte 30, an inner electrode 32 disposed on an inside surface of the solid electrolyte 30, an outer electrode 33 disposed on an outside surface of the solid electrode 30, a diffusion resistance layer 35 of porous ceramics disposed over the outer electrode 33, and a trap layer 36 disposed over the diffusion resistance layer 35 for trapping toxic substances.

To prohibit detection by other part than the air-fuel ratio detecting portion 39, an insulating layer 34 is provided between the solid electrolyte 30 and the outer electrode 33. The trap layer 36 has a thickness of 30 $\mu$m. Other structural details of the sensor 19 are substantially the same as those of the sensor 1 shown in FIG. 1.

By virtue of the relatively thick trap layer 36 (having a thickness not less than 10 $\mu$m), in an unburnt gas atmosphere, as it passes through the trap layer 36, undergoes complete combustion or burning. This prevents the vicinity of the electrodes 32, 33 from being enriched with oxygen and ensures that the measurement of an air-fuel ratio can be achieved with accuracy.

(Sixth Embodiment)

Figure 18:
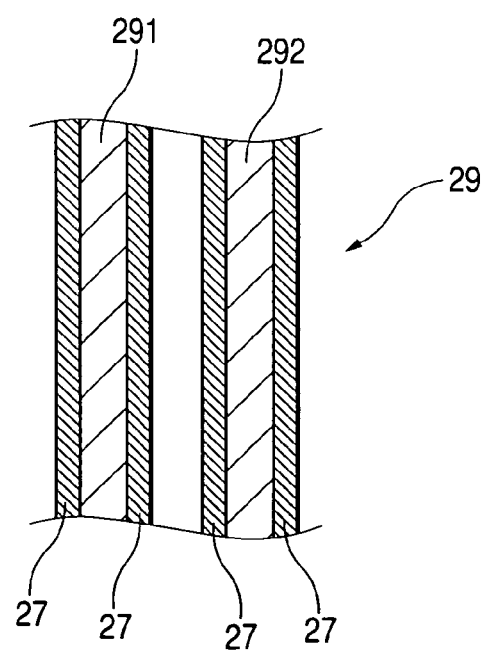
FIG. 18 is a cross-sectional view showing part of a measured gas side cover according to a further embodiment of the present invention.

FIG. 18 shows a modified form of the measured gas side cover 29 shown in FIG. 16. The modified measured gas side cover includes a catalytic layer 27 disposed over both surfaces (inside and outside surfaces) of each of the inner and outer cover members 291, 292.

The catalytic layer 27 is made of Pt and formed by baking a film of Pt paste applied or coated on the inside and outside surfaces of the inner and outer cover members 291, 292. By thus providing the catalytic layers 27, combustible gas contained in an unburnt gas atmosphere undergoes burning or combustion as it moves along the catalytic layers 27. The vicinity of the electrodes (not shown but identical to those 32, 33 shown in FIG. 17) is prevented from becoming oxygen-enriched.

(Seventh Embodiment)

Figure 19:
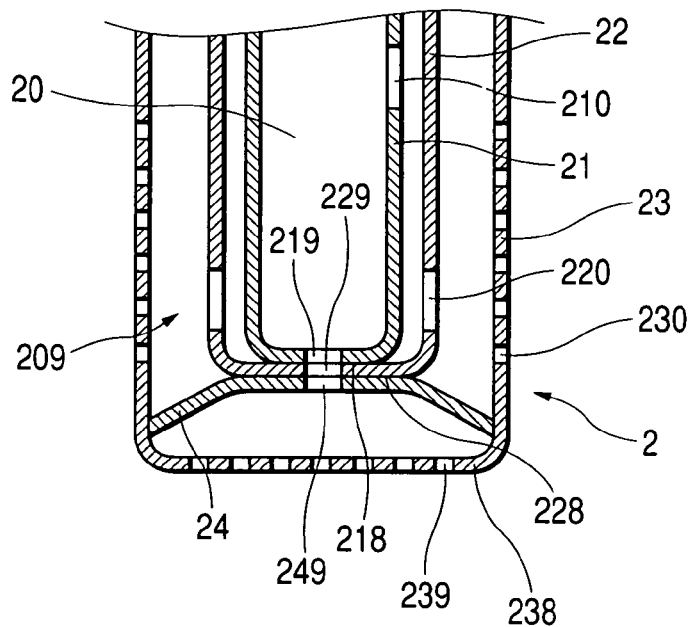
FIG. 19 is a cross-sectional view showing one form of a partition structure disposed inside the measured gas side cover.

Various forms of the partition structure 24 according to the present invention will be described with reference to FIGS. 19 through 23. Measured gas side covers 2 shown in FIGS. 19–23 are essentially the same in construction as the cover 2 shown in FIG. 2. The covers 2 are each composed of an inner cover member 21, an outer cover member 22 and an explosionproof cover member 23. A partition structure 24 is provided such that there is an annular inter-cover space 209 defined between the outer cover member 22 and the explosion cover member 23. With this arrangement, a gas to be measured is introduced from gas inlet holes 230 formed in a side wall (not designated) of the explosionproof cover member 23. The measured gas then passes successively through the gas inlet hole 220 of the outer cover member 22 and the gas inlet hole 210 of the inner cover member 21 and enters the measured gas chamber 20 (FIG. 19).

The measured gas side cover 2 shown in FIG. 19 has a partition structure 24 disposed therein. The partition structure 24 comprises a circular partition plate bent or formed into a dish-like configuration. The dish-like partition plate 24 has a flat central portion connected to the bottom wall 228 of the outer cover member 22 and an inclined outer peripheral portion extending radially outward from the central portion in an oblique downward direction so as to close a lower end of an annular inter-cover space 209 defined between the outer cover member 22 and the explosionproof cover member 23. The partition plate 24 has a central hole 249 formed at the center of the flat central portion and is connected end to end with the bottom hole 229 of the outer cover member 22.

Figure 20:
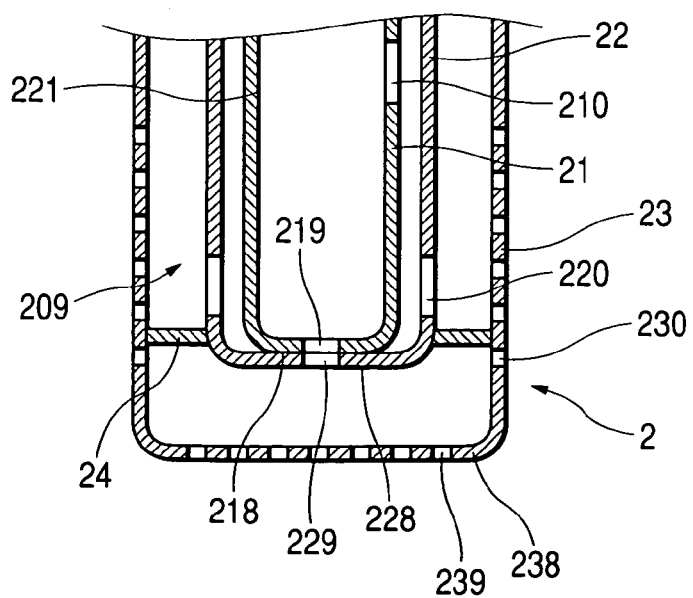
FIG. 20 is a view similar to FIG. 19, but showing a modified form of the partition structure incorporated in the measured gas side cover.

The measured gas side cover 2, shown in FIG. 20, has a partition structure 24 comprised of a flat circular ring hermetically fitted in an annular inter-cover space 208 defined between the outer cover member 22 and the explosionproof cover member 23 so as to close the annular space at a position slightly above the bottom wall 228 of the outer cover member 22. The circular ring 24 has an inner edge engaged with the side wall of the outer cover member 22 and an outer edge engaged with the side wall of the explosionproof cover member 23.

Figure 21:
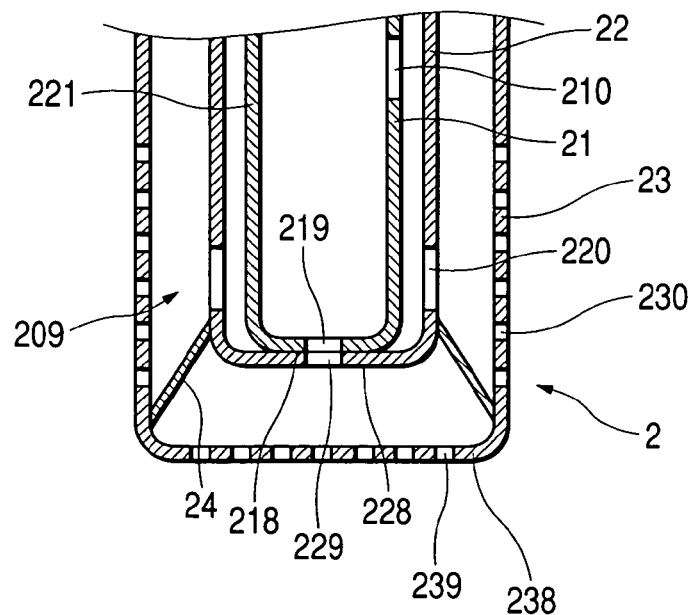
FIG. 21 is a view similar to FIG. 19, but showing another modified form of the partition structure incorporated in the measured gas side cover.

A partition structure 24 shown in FIG. 21 comprises a truncated hollow cone hermetically fitted in an annular inter-cover space 209 defined between the outer cover member 22 and the explosionproof cover member 23 so as to close the annular space 209 at a lower end portion thereof. The truncated hollow cone 24 has a small-diameter upper end engaged with the side wall 221 of the outer cover member 22 at a position slightly above the bottom wall 228, and a large-diameter lower end edge engaged with the side wall of the explosionproof cover member 23 at a position slightly above the bottom wall 238 of the explosionproof cover member 23.

Figure 22:
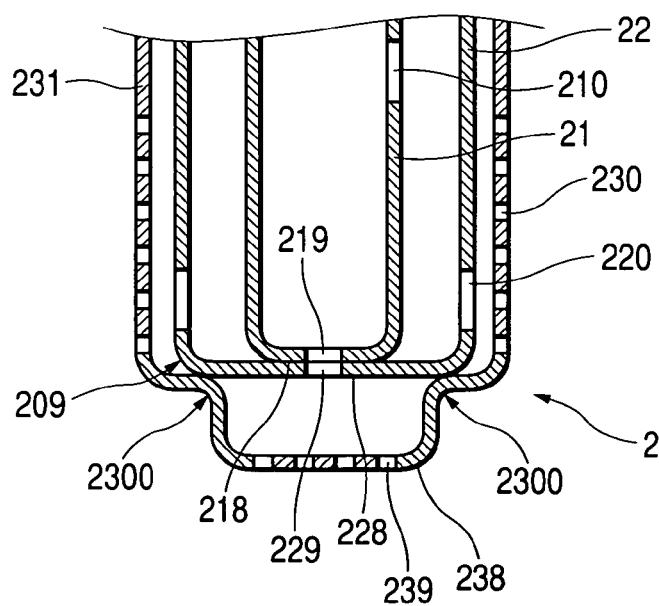
FIG. 22 is a view similar to FIG. 19, but showing a variant of the partition structure formed on a part of the measured gas side cover without using a separate partition member.

In the measured gas side cover 2 shown in FIG. 22, a lower part of the explosionproof cover member 23 is constricted in a radial inward direction such that the constricted part of the explosionproof cover member 23 is in close contact with the bottom wall 228 of the outer cover member 22 to thereby form a partition structure 2300. This structure is advantageous because no separate partition member is necessary.

Figure 23A:
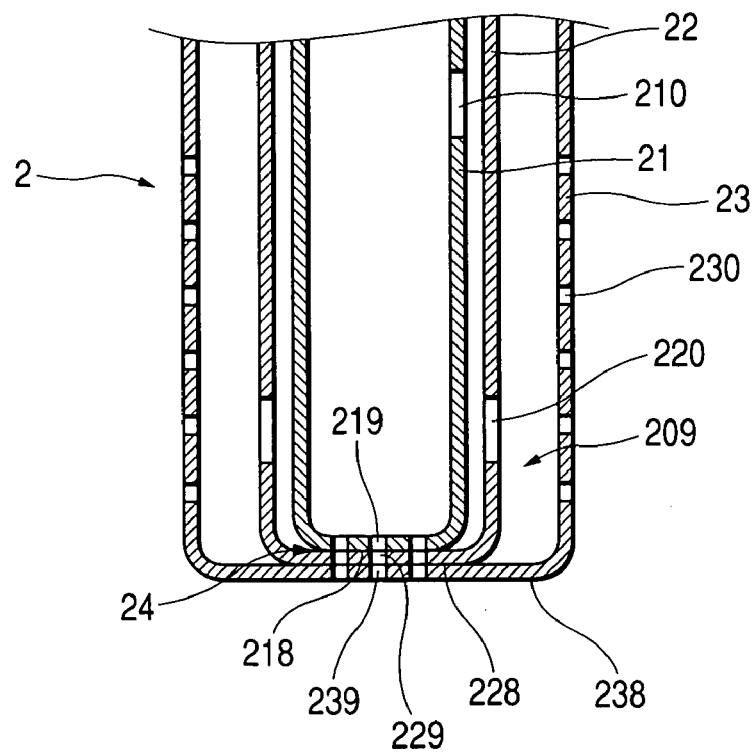
FIG. 23A is a view similar to FIG. 19, but showing another variant of the partition structure formed by the bottom walls of cover members that are connected or otherwise held in close contact with each other.
Figure 23B:
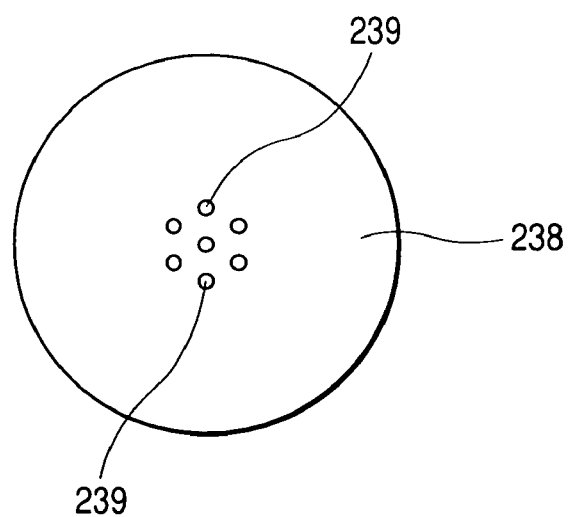
FIG. 23B is a bottom view showing the bottom wall of an explosionproof cover member.

FIG. 23A shows a partition structure 24 formed by the bottom walls 218, 228, 238 of the inner, outer and explosionproof cover members 21, 22, 23 that are connected or otherwise held in close contact with each other. To ensure that each bottom hole in one cover member is closed by one bottom hole in another cover member, the explosionproof cover member 23 has seven bottom holes 239, as shown in FIG. 23B. The bottom holes 239 serve, together with other cover members 21, 22, as explosion-proofing holes and have a diameter of 0.4 mm and a total area ranging from 0.3 to 12 mm². Bottom holes 219, 229 of the inner and outer cover members 21, 22 are arranged to match in position with the bottom holes 239 of the explosionproof cover member 23.

Figure 24A:
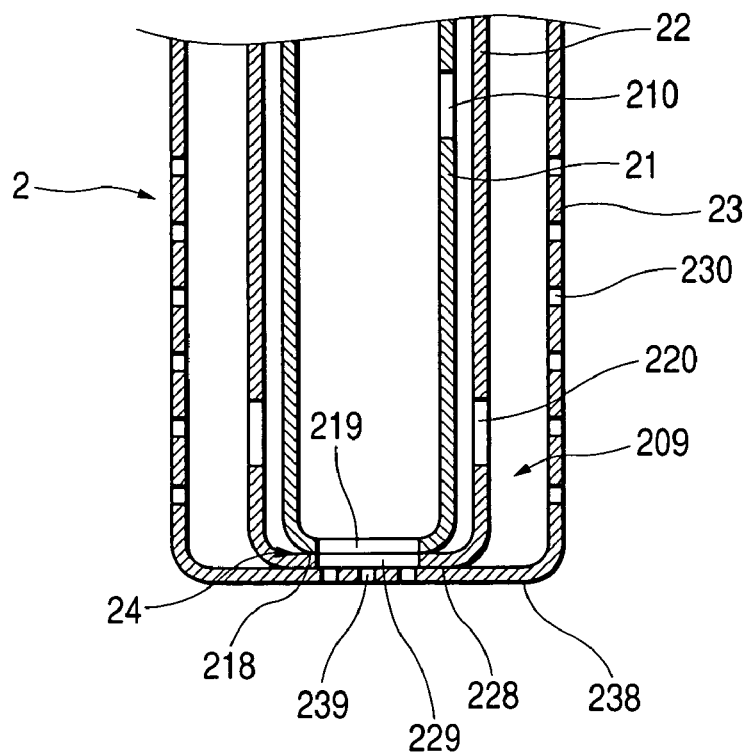
FIGS. 24A and 24B are views similar to FIGS. 23A and 23B, respectively, showing a modification according to the present invention.
Figure 24B:
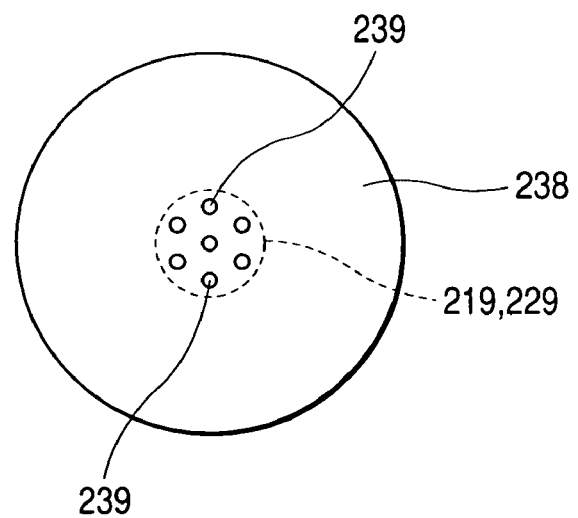

The measured gas side cover 2 shown in FIG. 24A is structurally the same as the cover 2 shown in FIG. 23A with the exception that as shown in FIG. 24B, the explosionproof cover member 23 has seven bottom holes 239 serving as explosion-proofing holes, while the inner and outer cover members 21, 22 have a single circular bottom hole 219, 229 formed at the center of the bottom wall 218, 228 of each cover member 21, 22. The circular bottom holes 219, 229 have a diameter of 7 mm, which is, determined so as not to close any of the bottom holes 239 of the explosionproof cover member 23.

In the measured gas side covers 2 shown in FIGS. 19–24, a measured gas introduced from the gas inlet holes 230 of the explosionproof cover member 23 is blocked from flowing into the bottom holes 239 because of the presence of the partition structure 24, 2300. Accordingly, the measured gas will pass through the gas inlet hole 220 of the outer cover member 22 and then moves into the inside chamber of the inner cover member 21 via the gas inlet hole 210 of the inner cover member 21.

The measured gas side covers shown in FIGS. 23 and 24 have relatively high thermal conductivity because the cover members 21, 22, 23 are directly connected together at the bottom walls 218, 228, 238 thereof. This might produce an undue increase in temperature of the explosionproof cover member. Since the measured gas side cover 2 is used with such a sensor designed for use in an unburnt gas atmosphere, it is necessary to control the temperature of the explosionproof cover member 23 below an explosion limit (for example, 257° C. as for gasoline).

Although in the illustrated embodiments the partition structures 24 have plate-like configurations, any other shape and configuration may be employed for the partition structure provided that it can block a flow of gas. For example, a meshed article disposed between the gas inlet hole and the bottom hole provides a certain degree of flow resistance and hence can be used as a partition structure.

Obviously, various minor changes and modifications are possible in the light of the above teaching. It is to be understood that within the scope of the appended claims the present invention may be practiced otherwise than as specifically described.

What is claimed is:

1. An air-fuel ratio sensor comprising:
   a cylindrical housing having a first end and an opposite second end;
   an air-fuel ratio sensor element inserted through the cylindrical housing and capable of detecting an air-fuel ratio in an atmosphere of unburnt gas, the sensor element having a detecting portion for performing detection of the air-fuel ratio;
   an atmospheric side cover disposed on the first end of the cylindrical housing and defining an inside chamber for storing therein atmospheric air; and
   a measured gas side cover disposed on the second end of the cylindrical housing so as to cover the air-fuel ratio sensor element and defining an inside chamber for storing therein a gas to be measured,
   wherein the measured gas side cover has a nested structure composed of a plurality of cup-shaped cover members disposed one inside another, each of the cup-shaped cover members having a gas inlet hole formed in a side wall thereof for introducing the measured gas into the inside chamber of the measured gas side cover, and a bottom hole formed in a bottom wall thereof,
   wherein the gas inlet hole of an innermost one of the plurality of cover members that directly faces the air-fuel ratio sensor element is offset from the detecting portion of the air-fuel ratio sensor element toward the housing in an axial direction of the air-fuel ratio sensor,
   wherein the cylindrical housing has an end face facing the inside chamber of the measured gas side cover at the second end of the housing, the detecting portion of the air-fuel ratio sensor element is spaced from the end face of the housing by a first distance in the axial direction of the sensor, and the gas inlet hole of the innermost cover member has a center located at a position spaced from the end face of the housing in the axial direction of the sensor by a second distance smaller than one-half of the first distance, and
   wherein the sensor is disposed in an exhaust manifold of a diesel engine for performing measurement of an air-fuel ratio in an exhaust gas containing a combustible gas added to on an exhaust side of the diesel engine.

2. The air-fuel ratio sensor according to claim 1, wherein the total area of the gas inlet hole of each cover member has a minimum value in the range of 0.3 to 12 mm².

3. The air-fuel ratio sensor according to claim 1, wherein the total area of the bottom hole of each cover member has a minimum value in the range of 0.3 to 12 mm².

4. The air-fuel ratio sensor according to claim 1, further comprising a partition structure for blocking flow communication of the measured gas between the gas inlet hole of each cover member and the bottom hole of each cover member.

5. The air-fuel ratio sensor according to claim 4, wherein the plurality of cover members of the measured gas side cover include an inner cover member forming the innermost cover member, an outer cover member disposed outside the inner cover member with a bottom wall thereof held in close contact with a bottom wall of the inner cover member, and an explosionproof cover disposed outside the outer cover member with a bottom wall thereof separated from the bottom wall of the outer cover member, the partition structure includes the bottom walls of the inner and outer cover members held in close contact with each other, and a partition plate hermetically fitted in the explosionproof cover member and adjacent to the bottom wall of the explosionproof cover member.

6. The air-fuel ratio sensor according to claim 5, wherein the partition plate has an outer peripheral portion extending obliquely from the bottom wall of the outer cover member toward the bottom wall of the explosionproof cover member.

7. The air-fuel ratio sensor according to claim 4, wherein the plurality of cover members of the measured gas side cover include an inner cover member forming the innermost cover member, an outer cover member disposed outside the inner cover member with a bottom wall thereof held in close contact with a bottom wall of the inner cover member, and an explosionproof cover disposed outside the outer cover member with a bottom wall thereof separated from the bottom wall of the outer cover member, and the partition structure includes the bottom walls of the inner and outer cover members held in close contact with each other, and a ring-shaped partition plate hermetically fitted in an annular space defined between the explosionproof cover member and the outer cover member and located adjacent to the bottom wall of the outer cover member.

8. The air-fuel ratio sensor according to claim 4, wherein the plurality of cover members of the measured gas side cover include an inner cover member forming the innermost cover member, an outer cover member disposed outside the inner cover member with a bottom wall thereof held in close contact with a bottom wall of the inner cover member, and an explosionproof cover disposed outside the outer cover member with a bottom wall thereof separated from the bottom wall of the outer cover member, and the partition structure includes the bottom walls of the inner and outer cover members held in close contact with each other, and a truncated hollow cone hermetically fitted in an annular space defined between the explosionproof cover member and the outer cover member and having a small diameter end engaged with a side wall the outer cover adjacent to the bottom wall of the outer cover member and an large diameter end engaged with a side wall of the explosionproof cover member adjacent to the bottom wall of the explosionproof cover member.

9. The air-fuel ratio sensor according to claim 4, wherein the plurality of cover members of the measured gas side cover include an inner cover member forming the innermost cover member, an outer cover member disposed outside the inner cover member with a bottom wall thereof held in close contact with a bottom wall of the inner cover member, and an explosionproof cover disposed outside the outer cover member with a bottom wall thereof separated from the bottom wall of the outer cover member, and the partition structure includes the bottom walls of the inner and outer cover members held in close contact with each other, and a part of a side wall of the explosionproof cover member being constricted in a radial inward direction so such that the constricted part of the side wall is in close contact with the bottom wall of the outer cover member.

10. The air-fuel ratio sensor according to claim 4, wherein the plurality of cover members of the measured gas side cover include an inner cover member forming the innermost cover member, an outer cover member disposed outside the inner cover member with a bottom wall thereof held in close contact with a bottom wall of the inner cover member, and an explosionproof cover disposed outside the outer cover member with a bottom wall thereof held in close contact with the bottom wall of the outer cover member, and the partition structure includes the bottom walls of the inner, outer and explosionproof cover members held in close contact with each other.

11. The air-fuel ratio sensor according to claim 1, wherein the plurality of cover members include an outer cover member disposed immediately outside the innermost cover member, and the gas inlet hole of the outer cover member is offset from the air-fuel ratio detecting portion of the sensor element in a direction away from the housing.

12. The air-fuel ratio sensor according to claim 1, wherein the air-fuel ratio sensor element comprises a cup-shaped sensor element or a laminated type sensor element.

13. The air-fuel ratio sensor according to claim 1, wherein the air-fuel ratio sensor element comprising a laminated type sensor element, and the plurality of cover members of the measured gas side cover each have a quadrangular shape in cross section.

14. An air-fuel ratio sensor, comprising:
a cylindrical housing having a first end and an opposite second end;
an air-fuel ratio sensor element inserted through the cylindrical housing and capable of detecting an air-fuel ratio in an atmosphere of unburnt gas, the sensor element having a detecting portion for performing detection of the air-fuel ratio;
an atmospheric side cover disposed on the first end of the cylindrical housing and defining an inside chamber for storing therein atmospheric air; and
a measured gas side cover disposed on the second end of the cylindrical housing so as to cover the air-fuel ratio sensor element and defining an inside chamber for storing therein a gas to be measured,
wherein the measured gas side cover has a nested structure composed of a plurality of cup-shaped cover members disposed one inside another, each of the cup-shaped cover members having a gas inlet hole formed in a side wall thereof for introducing the measured gas into the inside chamber of the measured gas side cover, and a bottom hole formed in a bottom wall thereof,
wherein the gas inlet hole of an innermost one of the plurality of cover members that directly faces the air-fuel ratio sensor element is offset from the detecting portion of the air-fuel ratio sensor element toward the housing in an axial direction of the air-fuel ratio sensor,
wherein the cylindrical housing has an end face facing the inside chamber of the measured gas side cover at the second end of the housing, the detecting portion of the air-fuel ratio sensor element is spaced from the end face of the housing by a first distance in the axial direction of the sensor, and the gas inlet hole of the innermost cover member has a center located at a position spaced from the end face of the housing in the axial direction of the sensor by a second distance smaller than one-half of the first distance, and
wherein the sensor is disposed in a surge tank for performing measurement of an air-fuel ratio in an evaporated gas.

15. An air-fuel ratio sensor comprising:
a cylindrical housing having a first end and an opposite second end;
an air-fuel ratio sensor element inserted through the cylindrical housing and capable of detecting an air-fuel ratio in an atmosphere of unburnt gas, the sensor element having a detecting portion for performing detection of the air-fuel ratio;
an atmospheric side cover disposed on the first end of the cylindrical housing and defining an inside chamber for storing therein atmospheric air; and
a measured gas side cover disposed on the second end of the cylindrical housing so as to cover the air-fuel ratio sensor element and defining an inside chamber for storing therein a gas to be measured, wherein the measured gas side cover has a nested structure composed of a plurality of cup-shaped cover members disposed one inside another, each of the cup-shaped cover members having a gas inlet hole formed in a side wall thereof for introducing the measured gas into the inside chamber of the measured gas side cover, and a bottom hole formed in a bottom wall thereof, and wherein the gas inlet hole of an innermost one of the plurality of cover members that directly faces the air-fuel ratio sensor element is offset from the detecting portion of the air-fuel ratio sensor element toward the housing in an axial direction of the air-fuel ratio sensor, and
a partition structure for blocking flow communication of the measured gas between the gas inlet hole of each cover member and the bottom hole of each cover member,
wherein the plurality of cover members of the measured gas side cover include an inner cover member forming the innermost cover member, an outer cover member disposed outside the inner cover member with a bottom wall thereof held in close contact with a bottom wall of the inner cover member, and an explosionproof cover disposed outside the outer cover member with a bottom wall thereof separated from the bottom wall of the outer cover member, the partition structure includes the bottom walls of the inner and outer cover members held in close contact with each other, and a partition plate hermetically fitted in the explosionproof cover member and adjacent to the bottom wall of the explosionproof cover member.

16. The air-fuel ratio sensor according to claim 15, wherein the partition plate has an outer peripheral portion extending obliquely from the bottom wall of the outer cover member toward the bottom wall of the explosionproof cover member.

17. An air-fuel ratio sensor comprising:
a cylindrical housing having a first end and an opposite second end;
an air-fuel ratio sensor element inserted through the cylindrical housing and capable of detecting an air-fuel ratio in an atmosphere of unburnt gas, the sensor element having a detecting portion for performing detection of the air-fuel ratio;
an atmospheric side cover disposed on the first end of the cylindrical housing and defining an inside chamber for storing therein atmospheric air; and
a measured gas side cover disposed on the second end of the cylindrical housing so as to cover the air-fuel ratio sensor element and defining an inside chamber for storing therein a gas to be measured, wherein the measured gas side cover has a nested structure composed of a plurality of cup-shaped cover members disposed one inside another, each of the cup-shaped cover members having a gas inlet hole formed in a side wall thereof for introducing the measured gas into the inside chamber of the measured gas side cover, and a bottom hole formed in a bottom wall thereof, and wherein the gas inlet hole of an innermost one of the plurality of cover members that directly faces the air-fuel ratio sensor element is offset from the detecting portion of the air-fuel ratio sensor element toward the housing in an axial direction of the air-fuel ratio sensor, and
a partition structure for blocking flow communication of the measured gas between the gas inlet hole of each cover member and the bottom hole of each cover member,
wherein the plurality of cover members of the measured gas side cover include an inner cover member forming the innermost cover member, an outer cover member disposed outside the inner cover member with a bottom wall thereof held in close contact with a bottom wall of the inner cover member, and an explosionproof cover disposed outside the outer cover member with a bottom wall thereof separated from the bottom wall of the outer cover member, and the partition structure includes the bottom walls of the inner and outer cover members held in close contact with each other, and a ring-shaped partition plate hermetically fitted in an annular space defined between the explosionproof cover member and the outer cover member and located adjacent to the bottom wall of the outer cover member.

18. An air-fuel ratio sensor comprising:
a cylindrical housing having a first end and an opposite second end;
an air-fuel ratio sensor element inserted through the cylindrical housing and capable of detecting an air-fuel ratio in an atmosphere of unburnt gas, the sensor element having a detecting portion for performing detection of the air-fuel ratio;
an atmospheric side cover disposed on the first end of the cylindrical housing and defining an inside chamber for storing therein atmospheric air; and
a measured gas side cover disposed on the second end of the cylindrical housing so as to cover the air-fuel ratio sensor element and defining an inside chamber for storing therein a gas to be measured, wherein the measured gas side cover has a nested structure composed of a plurality of cup-shaped cover members disposed one inside another, each of the cup-shaped cover members having a gas inlet hole formed in a side wall thereof for introducing the measured gas into the inside chamber of the measured gas side cover, and a bottom hole formed in a bottom wall thereof, and wherein the gas inlet hole of an innermost one of the plurality of cover members that directly faces the air-fuel ratio sensor element is offset from the detecting portion of the air-fuel ratio sensor element toward the housing in an axial direction of the air-fuel ratio sensor, and
a partition structure for blocking flow communication of the measured gas between the gas inlet hole of each cover member and the bottom hole of each cover member,
wherein the plurality of cover members of the measured gas side cover include an inner cover member forming the innermost cover member, an outer cover member disposed outside the inner cover member with a bottom wall thereof held in close contact with a bottom wall of the inner cover member, and an explosionproof cover disposed outside the outer cover member with a bottom wall thereof separated from the bottom wall of the outer cover member, and the partition structure includes the bottom walls of the inner and outer cover members held in close contact with each other, and a truncated hollow cone hermetically fitted in an annular space defined between the explosionproof cover member and the outer cover member and having a small diameter end engaged with a side wall the outer cover adjacent to the bottom wall of the outer cover member and an large diameter end engaged with a side wall of the explosionproof cover member adjacent to the bottom wall of the explosionproof cover member.

19. An air-fuel ratio sensor comprising:
a cylindrical housing having a first end and an opposite second end;
an air-fuel ratio sensor element inserted through the cylindrical housing and capable of detecting an air-fuel ratio in an atmosphere of unburnt gas, the sensor element having a detecting portion for performing detection of the air-fuel ratio;
an atmospheric side cover disposed on the first end of the cylindrical housing and defining an inside chamber for storing therein atmospheric air; and
a measured gas side cover disposed on the second end of the cylindrical housing so as to cover the air-fuel ratio sensor element and defining an inside chamber for storing therein a gas to be measured, wherein the measured gas side cover has a nested structure composed of a plurality of cup-shaped cover members disposed one inside another, each of the cup-shaped cover members having a gas inlet hole formed in a side wall thereof for introducing the measured gas into the inside chamber of the measured gas side cover, and a bottom hole formed in a bottom wall thereof, and wherein the gas inlet hole of an innermost one of the plurality of cover members that directly faces the air-fuel ratio sensor element is offset from the detecting portion of the air-fuel ratio sensor element toward the housing in an axial direction of the air-fuel ratio sensor, and
a partition structure for blocking flow communication of the measured gas between the gas inlet hole of each cover member and the bottom hole of each cover member,
wherein the plurality of cover members of the measured gas side cover include an inner cover member forming the innermost cover member, an outer cover member disposed outside the inner cover member with a bottom wall thereof held in close contact with a bottom wall of the inner cover member, and an explosionproof cover disposed outside the outer cover member with a bottom wall thereof separated from the bottom wall of the outer cover member, and the partition structure includes the bottom walls of the inner and outer cover members held in close contact with each other, and a part of a side wall of the explosionproof cover member being constricted in a radial inward direction so such that the constricted part of the side wall is in close contact with the bottom wall of the outer cover member.

20. An air-fuel ratio sensor comprising:
a cylindrical housing having a first end and an opposite second end;
an air-fuel ratio sensor element inserted through the cylindrical housing and capable of detecting an air-fuel ratio in an atmosphere of unburnt gas, the sensor element having a detecting portion for performing detection of the air-fuel ratio;
an atmospheric side cover disposed on the first end of the cylindrical housing and defining an inside chamber for storing therein atmospheric air; and
a measured gas side cover disposed on the second end of the cylindrical housing so as to cover the air-fuel ratio sensor element and defining an inside chamber for storing therein a gas to be measured, wherein the measured gas side cover has a nested structure composed of a plurality of cup-shaped cover members disposed one inside another, each of the cup-shaped cover members having a gas inlet hole formed in a side wall thereof for introducing the measured gas into the inside chamber of the measured gas side cover, and a bottom hole formed in a bottom wall thereof, and wherein the gas inlet hole of an innermost one of the plurality of cover members that directly faces the air-fuel ratio sensor element is offset from the detecting portion of the air-fuel ratio sensor element toward the housing in an axial direction of the air-fuel ratio sensor, and
a partition structure for blocking flow communication of the measured gas between the gas inlet hole of each cover member and the bottom hole of each cover member,
wherein the plurality of cover members of the measured gas side cover include an inner cover member forming the innermost cover member, an outer cover member disposed outside the inner cover member with a bottom wall thereof held in close contact with a bottom wall of the inner cover member, and an explosionproof cover disposed outside the outer cover member with a bottom wall thereof held in close contact with the bottom wall of the outer cover member, and the partition structure includes the bottom walls of the inner, outer and explosionproof cover members held in close contact with each other.

* * * * *